United States Patent
Loew

(10) Patent No.: US 10,041,064 B2
(45) Date of Patent: Aug. 7, 2018

(54) YEAST DISPLAY SYSTEMS

(71) Applicant: Andreas Loew, Somerville, MA (US)

(72) Inventor: Andreas Loew, Somerville, MA (US)

(73) Assignee: Novartis AG, Basel (CH)

( * ) Notice: Subject to any disclaimer, the term of this patent is extended or adjusted under 35 U.S.C. 154(b) by 216 days.

(21) Appl. No.: 15/135,438

(22) Filed: Apr. 21, 2016

(65) Prior Publication Data

US 2017/0081657 A1 Mar. 23, 2017

Related U.S. Application Data

(63) Continuation of application No. 13/139,332, filed as application No. PCT/EP2009/067066 on Dec. 14, 2009, now abandoned.

(60) Provisional application No. 61/122,910, filed on Dec. 16, 2008.

(51) Int. Cl.
| | |
|---|---|
| *C40B 30/04* | (2006.01) |
| *C12N 15/10* | (2006.01) |
| *C12N 15/81* | (2006.01) |
| *C40B 40/08* | (2006.01) |
| *C40B 50/06* | (2006.01) |
| *C07K 14/395* | (2006.01) |
| *C07K 14/78* | (2006.01) |

(52) U.S. Cl.
CPC ........ *C12N 15/1037* (2013.01); *C07K 14/395* (2013.01); *C07K 14/78* (2013.01); *C12N 15/81* (2013.01); *C12N 15/815* (2013.01); *C40B 40/08* (2013.01); *C40B 50/06* (2013.01); *C07K 2319/035* (2013.01); *C07K 2319/70* (2013.01); *C07K 2319/912* (2013.01); *C40B 30/04* (2013.01)

(58) Field of Classification Search
None
See application file for complete search history.

(56) References Cited

U.S. PATENT DOCUMENTS

| | | |
|---|---|---|
| 6,699,658 B1 | 3/2004 | Wittrup et al. |
| 7,309,575 B2 | 12/2007 | Kimple et al. |

FOREIGN PATENT DOCUMENTS

| | | |
|---|---|---|
| JP | 2002-508977 A | 3/2002 |
| JP | 2005-504541 A | 2/2005 |
| WO | 90/02809 A1 | 3/1990 |
| WO | 92/06191 A1 | 4/1992 |
| WO | 92/15605 A2 | 9/1992 |
| WO | 92/15677 A1 | 9/1992 |
| WO | 92/15679 A1 | 9/1992 |
| WO | 94/01567 A1 | 1/1994 |
| WO | 94/18330 A1 | 8/1994 |
| WO | 96/20278 A2 | 7/1996 |
| WO | 99/36569 A1 | 6/1999 |
| WO | 00/34784 A1 | 6/2000 |

(Continued)

OTHER PUBLICATIONS

Boder, Eric T. et al., "Yeast Surface Display for Screening Combinatorial Polypeptide Libraries", Nature Biotechnology (1997) vol. 15, pp. 553-557, Nature Publishing Group.

(Continued)

*Primary Examiner* — Christian C Boesen

(57) ABSTRACT

The present invention relates to the field of protein display libraries and library screening, In preferred embodiments, the present invention provides a three component system for display comprising a cell surface molecule, an adapter molecule and a display molecule.

28 Claims, 15 Drawing Sheets

(56) References Cited

FOREIGN PATENT DOCUMENTS

| WO | 01/64942 A1 | 9/2001 |
| WO | 02/32925 A2 | 4/2002 |
| WO | 02/085935 A1 | 10/2002 |
| WO | 03/029456 A1 | 4/2003 |
| WO | 03/066830 A2 | 8/2003 |
| WO | 2007/046825 A2 | 4/2007 |
| WO | 2007/130520 A2 | 11/2007 |
| WO | 2008/031098 A1 | 3/2008 |
| WO | 2008/066752 A2 | 6/2008 |
| WO | 2008/118476 A2 | 10/2008 |
| WO | 2008/130704 A2 | 10/2008 |
| WO | 2008/143954 A2 | 11/2008 |

OTHER PUBLICATIONS

Cebe, Regis et al., "Size of the Ligand Complex Between the N-Terminal Domain of the Gene III Coat Protein and the Non-Infective Phage Strongly Influences the Usefulness of In Vitro Selective Infective Phage Technology", Biochem J. (2000) vol. 352, pp. 841-849, Great Britain.

Kieke, Michelle C. et al., "Isolation of Anti-T Cell Receptor scFv Mutants by Yeast Surface Display", Protein Engineering (1997) vol. 10, No. 11, pp. 1303-1310.

European Opposition to Patent No. EP-B-2379718 (09774904.8), "Yeast Display Systems" in the name of Novartis AG. Opposed by Olswant LLP of London, UK. Opposite filed on Dec. 20, 2013, against Claims 1-19.

Rakestraw, J.A. et al., "A flow cytometric assay for screening improved heterologous protein secretion in yeast," Biotechnol Prog. Jul.-Aug. 2006;22(4):1200-8.

pYD1 Yeast Display Vector Kit. Manual [online]. Invotrogen, Dec. 10, 2002 [retrieved on Apr. 11, 2013]. Retrieved from the Internet: <URL:http://www.yribo.com/bioresource/sites/yrbio.com.bioresource/files/document/vector/1085/pyd1_man.pdf>.

Lipovsek, D. et al., "Evolution of an interloop disulfide bond in high-affinity antibody mimics based on fibronectin type III domain and selected by yeast surface display: molecular convergence with single-domain camelid and shark antibodies," J Mol Biol. May 11, 2007;368(4):1024-41.

Fuh, G. et al., "Analysis of PDZ domain-ligand interactions using carboxyl-terminal phage display," J Biol Chem. Jul. 14, 2000;275(28):21486-91.

Kimple, Michelle E. et al., "Affinity Tag for Protein Purification and Detection Based on the Disulfide-Linked Complex of InaD and NorpA," Sep. 2002, Biotechniques, 33, pp. 578-590.

Skerra, A., "Alternative non-antibody scaffolds for molecular recognition," Curr Opin Biotechnol. Aug. 2007; 18(4):295-304.

Daly, R. et al., "Expression of heterologous proteins in Pichia pastoris: a useful experimental tool in protein engineering and production," J Mol Recognit. Mar.-Apr. 2005;18(2):119-38.

European Opposition to Patent No. EP-B-2379718 (09774904.8), "Yeast Display Systems" in the name of Novartis AG. Opposed by Olswant LLP of London, UK. Opposition filed on Nov. 2, 2015, against Claims 1-19.

Hu, X. et al., "Yeast surface two-hybrid for quantitative in vivo detection of protein-protein interactions via the secretory pathway," J Biol Chem. Jun. 12, 2009;284(24):16369-76.

Jeong, K.J. et al., "APEx 2-hybrid a quantitative protein-protein interaction assay for antibody discovery and engineering," Proc Natl Acad Sci U S A. May 15, 2007;104(20):8247-52.

Weaver-Feldhaus, J.M. et al., "Yeast mating for combinatorial Fab library generation and surface display," FEBS Lett. Apr. 23, 2004;564(1-2):24-34.

Mazor, Y. et al., "Isolation of engineered, full-length antibodies from libraries expressed in *Escherichia coli*," Nat Biotechnol. May 2007;25(5):563-5.

Kondo, A. et al., "Yeast cell-surface display—application of molecular display," Appl Microbiol Biotechnol. Mar. 2004;64(1):28-40.

Kimple, Michelle E. et al., "Functional relevance of the disulfide-linked complex of the N-terminal PDZ domain of InaD with NorpA," EMBO J. Aug. 15, 2001;20(16):4414-22.

Pepper, L.R. et al., "A decade of yeast surface display technology: where are we now?" Comb Chem High Throughput Screen. Feb. 2008;11(2):127-34.

SEQUENCE LISTING

<160> NUMBER OF SEQ ID NOS: 13

<210> SEQ ID NO 1
<211> LENGTH: 24
<212> TYPE: PRT
<213> ORGANISM: Artificial Sequence
<220> FEATURE:
<223> OTHER INFORMATION: Saccharomyces cerevisiae

<400> SEQUENCE: 1

Met Leu Leu Gln Ala Phe Leu Phe Leu Leu Ala Gly Phe Ala Ala Lys
 1               5                  10                  15

Ile Ser Ala Asp Ala His Lys Ser
            20

<210> SEQ ID NO 2
<211> LENGTH: 725
<212> TYPE: PRT
<213> ORGANISM: Artificial Sequence
<220> FEATURE:
<223> OTHER INFORMATION: pPIC3.5 AGA1

<400> SEQUENCE: 2

Met Thr Leu Ser Phe Ala His Phe Thr Tyr Leu Phe Thr Ile Leu Leu
 1               5                  10                  15

Gly Leu Thr Asn Ile Ala Leu Ala Ser Asp Pro Glu Thr Ile Leu Val
            20                  25                  30

Thr Ile Thr Lys Thr Asn Asp Ala Asn Gly Val Val Thr Thr Thr Val
        35                  40                  45

Ser Pro Ala Leu Val Ser Thr Ser Thr Ile Val Gln Ala Gly Thr Thr
 50                  55                  60

Thr Leu Tyr Thr Thr Trp Cys Pro Leu Thr Val Ser Thr Ser Ser Ala
65                  70                  75                  80

Ala Glu Ile Ser Pro Ser Ile Ser Tyr Ala Thr Thr Leu Ser Arg Phe
                85                  90                  95

Ser Thr Leu Thr Leu Ser Thr Glu Val Cys Ser His Glu Ala Cys Pro
            100                 105                 110

Ser Ser Ser Thr Leu Pro Thr Thr Thr Leu Ser Val Thr Ser Lys Phe
        115                 120                 125

Thr Ser Tyr Ile Cys Pro Thr Cys His Thr Thr Ala Ile Ser Ser Leu
130                 135                 140

Ser Glu Val Gly Thr Thr Thr Val Val Ser Ser Ser Ala Ile Glu Pro
145                 150                 155                 160

Ser Ser Ala Ser Ile Ile Ser Pro Val Thr Ser Thr Leu Ser Ser Thr
                165                 170                 175

Thr Ser Ser Asn Pro Thr Thr Thr Ser Leu Ser Ser Thr Ser Thr Ser
            180                 185                 190

Pro Ser Ser Thr Ser Thr Ser Pro Ser Ser Thr Ser Ser Ser Ser Ser
        195                 200                 205

Ser Thr Ser Thr Ser Ser Ser Thr Ser Thr Ser Ser Ser Ser Ser Thr
210                 215                 220

Ser Thr Ser Pro Ser Ser Thr Ser Thr Ser Ser Leu Thr Ser Thr
225                 230                 235                 240

Ser Ser Ser Ser Thr Ser Ser Gln Ser Ser Thr Ser Thr Thr Ser Ser
                245                 250                 255

Ser Ser Ser Ser Thr Ser Pro Ser Ser Thr Ser Thr Ser Ser Ser Ser
            260                 265                 270

```
Thr Ser Thr Ser Pro Ser Ser Lys Ser Thr Ser Ala Ser Ser Thr Ser
            275                 280                 285

Thr Ser Ser Tyr Ser Thr Ser Thr Ser Pro Ser Leu Thr Ser Ser Ser
        290                 295                 300

Pro Thr Leu Ala Ser Thr Ser Pro Ser Ser Thr Ser Ile Ser Ser Thr
305                     310                 315                 320

Phe Thr Asp Ser Thr Ser Ser Leu Gly Ser Ser Ile Ala Ser Ser Ser
            325                 330                 335

Thr Ser Val Ser Leu Tyr Ser Pro Ser Thr Pro Val Tyr Ser Val Pro
                340                 345                 350

Ser Thr Ser Ser Asn Val Ala Thr Pro Ser Met Thr Ser Ser Thr Val
        355                 360                 365

Glu Thr Thr Val Ser Ser Gln Ser Ser Ser Glu Tyr Ile Thr Lys Ser
    370                 375                 380

Ser Ile Ser Thr Thr Ile Pro Ser Phe Ser Met Ser Thr Tyr Phe Thr
385                 390                 395                 400

Thr Val Ser Gly Val Thr Thr Met Tyr Thr Thr Trp Cys Pro Tyr Ser
                405                 410                 415

Ser Glu Ser Glu Thr Ser Thr Leu Thr Ser Met His Glu Thr Val Thr
            420                 425                 430

Thr Asp Ala Thr Val Cys Thr His Glu Ser Cys Met Pro Ser Gln Thr
        435                 440                 445

Thr Ser Leu Ile Thr Ser Ser Ile Lys Met Ser Thr Lys Asn Val Ala
    450                 455                 460

Thr Ser Val Ser Thr Ser Thr Val Glu Ser Ser Tyr Ala Cys Ser Thr
465                 470                 475                 480

Cys Ala Glu Thr Ser His Ser Tyr Ser Ser Val Gln Thr Ala Ser Ser
                485                 490                 495

Ser Ser Val Thr Gln Gln Thr Thr Ser Thr Lys Ser Trp Val Ser Ser
        500                 505                 510

Met Thr Thr Ser Asp Glu Asp Phe Asn Lys His Ala Thr Gly Lys Tyr
    515                 520                 525

His Val Thr Ser Ser Gly Thr Ser Thr Ile Ser Thr Ser Val Ser Glu
        530                 535                 540

Ala Thr Ser Thr Ser Ser Ile Asp Ser Glu Ser Gln Glu Gln Ser Ser
545                 550                 555                 560

His Leu Leu Ser Thr Ser Val Leu Ser Ser Ser Leu Ser Ala Thr
                565                 570                 575

Leu Ser Ser Asp Ser Thr Ile Leu Leu Phe Ser Ser Val Ser Ser Leu
            580                 585                 590

Ser Val Glu Gln Ser Pro Val Thr Thr Leu Gln Ile Ser Ser Thr Ser
        595                 600                 605

Glu Ile Leu Gln Pro Thr Ser Ser Thr Ala Ile Ala Thr Ile Ser Ala
610                 615                 620

Ser Thr Ser Ser Leu Ser Ala Thr Ser Ile Ser Thr Pro Ser Thr Ser
625                 630                 635                 640

Val Glu Ser Thr Ile Glu Ser Ser Leu Thr Pro Thr Val Ser Ser
                645                 650                 655

Ile Phe Leu Ser Ser Ser Ser Ala Pro Ser Ser Leu Gln Thr Ser Val
            660                 665                 670

Thr Thr Thr Glu Val Ser Thr Thr Ser Ile Ser Ile Gln Tyr Gln Thr
        675                 680                 685

Ser Ser Met Val Thr Ile Ser Gln Tyr Met Gly Ser Gly Ser Gln Thr
```

```
                690                 695                 700
Arg Leu Pro Leu Gly Lys Leu Val Phe Ala Ile Met Ala Val Ala Cys
705                 710                 715                 720

Asn Val Ile Phe Ser
            725
```

<210> SEQ ID NO 3
<211> LENGTH: 232
<212> TYPE: PRT
<213> ORGANISM: Artificial Sequence
<220> FEATURE:
<223> OTHER INFORMATION: pPIC6 A AGA2-InaD

<400> SEQUENCE: 3

```
Met Gln Leu Leu Arg Cys Phe Ser Ile Phe Ser Val Ile Ala Ser Val
1               5                   10                  15

Leu Ala Gln Glu Leu Thr Thr Ile Cys Glu Gln Ile Pro Ser Pro Thr
            20                  25                  30

Leu Glu Ser Thr Pro Tyr Ser Leu Ser Thr Thr Thr Ile Leu Ala Asn
        35                  40                  45

Gly Lys Ala Met Gln Gly Val Phe Glu Tyr Tyr Lys Ser Val Thr Phe
50                  55                  60

Val Ser Asn Cys Gly Ser His Pro Ser Thr Thr Ser Lys Gly Ser Pro
65                  70                  75                  80

Ile Asn Thr Gln Tyr Val Phe Lys Leu Leu Gln Ala Ser Gly Gly Gly
                85                  90                  95

Gly Ser Gly Gly Gly Gly Ser Gly Gly Gly Gly Ser Ala Ser Met Thr
            100                 105                 110

Gly Gly Gln Gln Met Gly Arg Glu Asn Leu Tyr Phe Gln Gly Val Pro
        115                 120                 125

Gly Ser Ser Val Val Ser Arg Ala Gly Glu Leu Ile His Met Val Thr
130                 135                 140

Leu Asp Lys Thr Gly Lys Lys Ser Phe Gly Ile Cys Ile Val Arg Gly
145                 150                 155                 160

Glu Val Lys Asp Ser Pro Asn Thr Lys Thr Thr Gly Ile Phe Ile Lys
                165                 170                 175

Gly Ile Val Pro Asp Ser Pro Ala His Leu Cys Gly Arg Leu Lys Val
            180                 185                 190

Gly Asp Arg Ile Leu Ser Leu Asn Gly Lys Asp Val Arg Asn Ser Thr
        195                 200                 205

Glu Gln Ala Val Ile Asp Leu Ile Lys Glu Ala Asp Phe Lys Ile Glu
    210                 215                 220

Leu Glu Ile Gln Thr Phe Asp Lys
225                 230
```

<210> SEQ ID NO 4
<211> LENGTH: 186
<212> TYPE: PRT
<213> ORGANISM: Artificial Sequence
<220> FEATURE:
<223> OTHER INFORMATION: pPICHOLI-1_MFalpha1Hsa-Fn10-NorpA

<400> SEQUENCE: 4

```
Met Lys Trp Val Ser Phe Ile Ser Leu Leu Phe Leu Phe Ser Ser Ala
1               5                   10                  15

Tyr Ser Arg Ser Leu Asp Lys Arg Glu Asn Leu Tyr Phe Gln Gly Gly
            20                  25                  30
```

Ser Val Ser Asp Val Pro Arg Asp Leu Glu Val Val Ala Ala Thr Pro
        35                  40                  45

Thr Ser Leu Leu Ile Ser Trp Asp Ala Pro Ala Val Thr Val Arg Tyr
 50                  55                  60

Tyr Arg Ile Thr Tyr Gly Glu Thr Gly Gly Asn Ser Pro Val Gln Glu
 65                  70                  75                  80

Phe Thr Val Pro Gly Ser Lys Ser Thr Ala Thr Ile Ser Gly Leu Lys
                 85                  90                  95

Pro Gly Val Asp Tyr Thr Ile Thr Val Tyr Ala Val Thr Gly Arg Gly
            100                 105                 110

Asp Ser Pro Ala Ser Ser Lys Pro Ile Ser Ile Asn Tyr Arg Thr Glu
            115                 120                 125

Phe Glu Asn Leu Tyr Phe Gln Gly Ser Gly Gly Gly Gly Glu Gln Lys
130                 135                 140

Leu Ile Ser Glu Glu Asp Leu His His His His His His Pro Ser Thr
145                 150                 155                 160

Pro Pro Thr Pro Ser Pro Ser Thr Pro Pro Thr Pro Ser Pro Ser Tyr
                165                 170                 175

Lys Thr Gln Gly Lys Thr Glu Phe Cys Ala
            180                 185

<210> SEQ ID NO 5
<211> LENGTH: 186
<212> TYPE: PRT
<213> ORGANISM: Artificial Sequence
<220> FEATURE:
<223> OTHER INFORMATION: pPICHOLI-C MfalphalHsa-Fn10-NorpA

<400> SEQUENCE: 5

Met Lys Trp Val Ser Phe Ile Ser Leu Leu Phe Leu Phe Ser Ser Ala
 1               5                  10                  15

Tyr Ser Arg Ser Leu Asp Lys Arg Glu Asn Leu Tyr Phe Gln Gly Gly
             20                  25                  30

Ser Val Ser Asp Val Pro Arg Asp Leu Glu Val Val Ala Ala Thr Pro
        35                  40                  45

Thr Ser Leu Leu Ile Ser Trp Asp Ala Pro Ala Val Thr Val Arg Tyr
 50                  55                  60

Tyr Arg Ile Thr Tyr Gly Glu Thr Gly Gly Asn Ser Pro Val Gln Glu
 65                  70                  75                  80

Phe Thr Val Pro Gly Ser Lys Ser Thr Ala Thr Ile Ser Gly Leu Lys
                 85                  90                  95

Pro Gly Val Asp Tyr Thr Ile Thr Val Tyr Ala Val Thr Gly Arg Gly
            100                 105                 110

Asp Ser Pro Ala Ser Ser Lys Pro Ile Ser Ile Asn Tyr Arg Thr Glu
            115                 120                 125

Phe Glu Asn Leu Tyr Phe Gln Gly Ser Gly Gly Gly Gly Glu Gln Lys
130                 135                 140

Leu Ile Ser Glu Glu Asp Leu His His His His His His Pro Ser Thr
145                 150                 155                 160

Pro Pro Thr Pro Ser Pro Ser Thr Pro Pro Thr Pro Ser Pro Ser Tyr
                165                 170                 175

Lys Thr Gln Gly Lys Thr Glu Phe Cys Ala
            180                 185

<210> SEQ ID NO 6
<211> LENGTH: 232

```
<212> TYPE: PRT
<213> ORGANISM: Artificial Sequence
<220> FEATURE:
<223> OTHER INFORMATION: pYD_NBC1_Aga2-InaD

<400> SEQUENCE: 6
```

| Met | Gln | Leu | Leu | Arg | Cys | Phe | Ser | Ile | Phe | Ser | Val | Ile | Ala | Ser | Val |
|---|---|---|---|---|---|---|---|---|---|---|---|---|---|---|---|
| 1 | | | | 5 | | | | | 10 | | | | | 15 | |

| Leu | Ala | Gln | Glu | Leu | Thr | Thr | Ile | Cys | Glu | Gln | Ile | Pro | Ser | Pro | Thr |
|---|---|---|---|---|---|---|---|---|---|---|---|---|---|---|---|
| | | | 20 | | | | | 25 | | | | | 30 | | |

| Leu | Glu | Ser | Thr | Pro | Tyr | Ser | Leu | Ser | Thr | Thr | Thr | Ile | Leu | Ala | Asn |
|---|---|---|---|---|---|---|---|---|---|---|---|---|---|---|---|
| | | | 35 | | | | | 40 | | | | | 45 | | |

| Gly | Lys | Ala | Met | Gln | Gly | Val | Phe | Glu | Tyr | Tyr | Lys | Ser | Val | Thr | Phe |
|---|---|---|---|---|---|---|---|---|---|---|---|---|---|---|---|
| 50 | | | | | 55 | | | | | 60 | | | | | |

| Val | Ser | Asn | Cys | Gly | Ser | His | Pro | Ser | Thr | Thr | Ser | Lys | Gly | Ser | Pro |
|---|---|---|---|---|---|---|---|---|---|---|---|---|---|---|---|
| 65 | | | | | 70 | | | | | 75 | | | | | 80 |

| Ile | Asn | Thr | Gln | Tyr | Val | Phe | Lys | Leu | Leu | Gln | Ala | Ser | Gly | Gly | Gly |
|---|---|---|---|---|---|---|---|---|---|---|---|---|---|---|---|
| | | | | 85 | | | | | 90 | | | | | 95 | |

| Gly | Ser | Gly | Gly | Gly | Gly | Ser | Gly | Gly | Gly | Ser | Ala | Ser | Met | Thr |
|---|---|---|---|---|---|---|---|---|---|---|---|---|---|---|
| | | | 100 | | | | | 105 | | | | | 110 | |

| Gly | Gly | Gln | Gln | Met | Gly | Arg | Glu | Asn | Leu | Tyr | Phe | Gln | Gly | Val | Pro |
|---|---|---|---|---|---|---|---|---|---|---|---|---|---|---|---|
| | | | 115 | | | | | 120 | | | | | 125 | | |

| Gly | Ser | Ser | Val | Val | Ser | Arg | Ala | Gly | Glu | Leu | Ile | His | Met | Val | Thr |
|---|---|---|---|---|---|---|---|---|---|---|---|---|---|---|---|
| | 130 | | | | | 135 | | | | | 140 | | | | |

| Leu | Asp | Lys | Thr | Gly | Lys | Lys | Ser | Phe | Gly | Ile | Cys | Ile | Val | Arg | Gly |
|---|---|---|---|---|---|---|---|---|---|---|---|---|---|---|---|
| 145 | | | | | 150 | | | | | 155 | | | | | 160 |

| Glu | Val | Lys | Asp | Ser | Pro | Asn | Thr | Lys | Thr | Thr | Gly | Ile | Phe | Ile | Lys |
|---|---|---|---|---|---|---|---|---|---|---|---|---|---|---|---|
| | | | | 165 | | | | | 170 | | | | | 175 | |

| Gly | Ile | Val | Pro | Asp | Ser | Pro | Ala | His | Leu | Cys | Gly | Arg | Leu | Lys | Val |
|---|---|---|---|---|---|---|---|---|---|---|---|---|---|---|---|
| | | | 180 | | | | | 185 | | | | | 190 | | |

| Gly | Asp | Arg | Ile | Leu | Ser | Leu | Asn | Gly | Lys | Asp | Val | Arg | Asn | Ser | Thr |
|---|---|---|---|---|---|---|---|---|---|---|---|---|---|---|---|
| | | 195 | | | | | 200 | | | | | 205 | | | |

| Glu | Gln | Ala | Val | Ile | Asp | Leu | Ile | Lys | Glu | Ala | Asp | Phe | Lys | Ile | Glu |
|---|---|---|---|---|---|---|---|---|---|---|---|---|---|---|---|
| | 210 | | | | | 215 | | | | | 220 | | | | |

| Leu | Glu | Ile | Gln | Thr | Phe | Asp | Lys |
|---|---|---|---|---|---|---|---|
| 225 | | | | | 230 | | |

```
<210> SEQ ID NO 7
<211> LENGTH: 186
<212> TYPE: PRT
<213> ORGANISM: Artificial Sequence
<220> FEATURE:
<223> OTHER INFORMATION: pYS6/CT_HSA_MFalpha1_Fn10_NorpA

<400> SEQUENCE: 7
```

| Met | Lys | Trp | Val | Ser | Phe | Ile | Ser | Leu | Leu | Phe | Leu | Phe | Ser | Ser | Ala |
|---|---|---|---|---|---|---|---|---|---|---|---|---|---|---|---|
| 1 | | | | 5 | | | | | 10 | | | | | 15 | |

| Tyr | Ser | Arg | Ser | Leu | Asp | Lys | Arg | Glu | Asn | Leu | Tyr | Phe | Gln | Gly | Gly |
|---|---|---|---|---|---|---|---|---|---|---|---|---|---|---|---|
| | | | 20 | | | | | 25 | | | | | 30 | | |

| Ser | Val | Ser | Asp | Val | Pro | Arg | Asp | Leu | Glu | Val | Val | Ala | Ala | Thr | Pro |
|---|---|---|---|---|---|---|---|---|---|---|---|---|---|---|---|
| | | 35 | | | | | 40 | | | | | 45 | | | |

| Thr | Ser | Leu | Leu | Ile | Ser | Trp | Asp | Ala | Pro | Ala | Val | Thr | Val | Arg | Tyr |
|---|---|---|---|---|---|---|---|---|---|---|---|---|---|---|---|
| | 50 | | | | | 55 | | | | | 60 | | | | |

| Tyr | Arg | Ile | Thr | Tyr | Gly | Glu | Thr | Gly | Gly | Asn | Ser | Pro | Val | Gln | Glu |
|---|---|---|---|---|---|---|---|---|---|---|---|---|---|---|---|
| 65 | | | | | 70 | | | | | 75 | | | | | 80 |

| Phe | Thr | Val | Pro | Gly | Ser | Lys | Ser | Thr | Ala | Thr | Ile | Ser | Gly | Leu | Lys |
|---|---|---|---|---|---|---|---|---|---|---|---|---|---|---|---|
| | | | | 85 | | | | | 90 | | | | | 95 | |

```
Pro Gly Val Asp Tyr Thr Ile Thr Val Tyr Ala Val Thr Gly Arg Gly
            100                 105                 110

Asp Ser Pro Ala Ser Ser Lys Pro Ile Ser Ile Asn Tyr Arg Thr Glu
        115                 120                 125

Phe Glu Asn Leu Tyr Phe Gln Gly Ser Gly Gly Gly Gly Gln Lys
    130                 135                 140

Leu Ile Ser Glu Glu Asp Leu His His His His His His Pro Ser Thr
145                 150                 155                 160

Pro Pro Thr Pro Ser Pro Ser Thr Pro Pro Thr Pro Ser Pro Ser Tyr
                165                 170                 175

Lys Thr Gln Gly Lys Thr Glu Phe Cys Ala
            180                 185

<210> SEQ ID NO 8
<211> LENGTH: 97
<212> TYPE: PRT
<213> ORGANISM: Unknown
<220> FEATURE:
<223> OTHER INFORMATION: InaD PDZ domain amino acid sequence

<400> SEQUENCE: 8

Ala Gly Glu Leu Ile His Met Val Thr Leu Asp Lys Thr Gly Lys Lys
1               5                   10                  15

Ser Phe Gly Ile Cys Ile Val Arg Gly Glu Val Lys Asp Ser Pro Asn
            20                  25                  30

Thr Lys Thr Thr Gly Ile Phe Ile Lys Gly Ile Val Pro Asp Ser Pro
        35                  40                  45

Ala His Leu Cys Gly Arg Leu Lys Val Gly Asp Arg Ile Leu Ser Leu
    50                  55                  60

Asn Gly Lys Asp Val Arg Asn Ser Thr Glu Gln Ala Val Ile Asp Leu
65                  70                  75                  80

Ile Lys Glu Ala Asp Phe Lys Ile Glu Leu Glu Ile Gln Thr Phe Asp
                85                  90                  95

Lys

<210> SEQ ID NO 9
<211> LENGTH: 11
<212> TYPE: PRT
<213> ORGANISM: Unknown
<220> FEATURE:
<223> OTHER INFORMATION: NorpA C-terminal

<400> SEQUENCE: 9

Tyr Lys Thr Gln Gly Lys Thr Glu Phe Cys Ala
1               5                   10

<210> SEQ ID NO 10
<211> LENGTH: 737
<212> TYPE: PRT
<213> ORGANISM: Artificial Sequence
<220> FEATURE:
<223> OTHER INFORMATION: pYS6/CT* MFalpha HSA-NorpA

<400> SEQUENCE: 10

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
```

```
            35                  40                  45
Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Ala Ser Asp Ala His Lys Ser
                85                  90                  95

Glu Val Ala His Arg Phe Lys Asp Leu Gly Glu Glu Asn Phe Lys Ala
            100                 105                 110

Leu Val Leu Ile Ala Phe Ala Gln Tyr Leu Gln Gln Cys Pro Phe Glu
        115                 120                 125

Asp His Val Lys Leu Val Asn Glu Val Thr Glu Phe Ala Lys Thr Cys
    130                 135                 140

Val Ala Asp Glu Ser Ala Glu Asn Cys Asp Lys Ser Leu His Thr Leu
145                 150                 155                 160

Phe Gly Asp Lys Leu Cys Thr Val Ala Thr Leu Arg Glu Thr Tyr Gly
                165                 170                 175

Glu Met Ala Asp Cys Cys Ala Lys Gln Glu Pro Glu Arg Asn Glu Cys
            180                 185                 190

Phe Leu Gln His Lys Asp Asp Asn Pro Asn Leu Pro Arg Leu Val Arg
        195                 200                 205

Pro Glu Val Asp Val Met Cys Thr Ala Phe His Asp Asn Glu Glu Thr
    210                 215                 220

Phe Leu Lys Lys Tyr Leu Tyr Glu Ile Ala Arg Arg His Pro Tyr Phe
225                 230                 235                 240

Tyr Ala Pro Glu Leu Leu Phe Phe Ala Lys Arg Tyr Lys Ala Ala Phe
                245                 250                 255

Thr Glu Cys Cys Gln Ala Ala Asp Lys Ala Ala Cys Leu Leu Pro Lys
            260                 265                 270

Leu Asp Glu Leu Arg Asp Glu Gly Lys Ala Ser Ser Ala Lys Gln Arg
        275                 280                 285

Leu Lys Cys Ala Ser Leu Gln Lys Phe Gly Glu Arg Ala Phe Lys Ala
    290                 295                 300

Trp Ala Val Ala Arg Leu Ser Gln Arg Phe Pro Lys Ala Glu Phe Ala
305                 310                 315                 320

Glu Val Ser Lys Leu Val Thr Asp Leu Thr Lys Val His Thr Glu Cys
                325                 330                 335

Cys His Gly Asp Leu Leu Glu Cys Ala Asp Asp Arg Ala Asp Leu Ala
            340                 345                 350

Lys Tyr Ile Cys Glu Asn Gln Asp Ser Ile Ser Ser Lys Leu Lys Glu
        355                 360                 365

Cys Cys Glu Lys Pro Leu Leu Glu Lys Ser His Cys Ile Ala Glu Val
    370                 375                 380

Glu Asn Asp Glu Met Pro Ala Asp Leu Pro Ser Leu Ala Ala Asp Phe
385                 390                 395                 400

Val Glu Ser Lys Asp Val Cys Lys Asn Tyr Ala Glu Ala Lys Asp Val
                405                 410                 415

Phe Leu Gly Met Phe Leu Tyr Glu Tyr Ala Arg Arg His Pro Asp Tyr
            420                 425                 430

Ser Val Val Leu Leu Leu Arg Leu Ala Lys Thr Tyr Glu Thr Thr Leu
        435                 440                 445

Glu Lys Cys Cys Ala Ala Ala Asp Pro His Glu Cys Tyr Ala Lys Val
    450                 455                 460
```

```
Phe Asp Glu Phe Lys Pro Leu Val Glu Pro Gln Asn Leu Ile Lys
465                 470                 475                 480

Gln Asn Cys Glu Leu Phe Glu Gln Leu Gly Glu Tyr Lys Phe Gln Asn
            485                 490                 495

Ala Leu Leu Val Arg Tyr Thr Lys Lys Val Pro Gln Val Ser Thr Pro
                500                 505                 510

Thr Leu Val Glu Val Ser Arg Asn Leu Gly Lys Val Gly Ser Lys Cys
            515                 520                 525

Cys Lys His Pro Glu Ala Lys Arg Met Pro Cys Ala Glu Asp Tyr Leu
530                 535                 540

Ser Val Val Leu Asn Gln Leu Cys Val Leu His Glu Lys Thr Pro Val
545                 550                 555                 560

Ser Asp Arg Val Thr Lys Cys Cys Thr Glu Ser Leu Val Asn Arg Arg
                565                 570                 575

Pro Cys Phe Ser Ala Leu Glu Val Asp Glu Thr Tyr Val Pro Lys Glu
            580                 585                 590

Phe Asn Ala Glu Thr Phe Thr Phe His Ala Asp Ile Cys Thr Leu Ser
            595                 600                 605

Glu Lys Glu Arg Gln Ile Lys Lys Gln Thr Ala Leu Val Glu Leu Val
610                 615                 620

Lys His Lys Pro Lys Ala Thr Lys Glu Gln Leu Lys Ala Val Met Asp
625                 630                 635                 640

Asp Phe Ala Ala Phe Val Glu Lys Cys Cys Lys Ala Asp Asp Lys Glu
                645                 650                 655

Thr Cys Phe Ala Glu Glu Gly Lys Lys Leu Val Ala Ala Ser Gln Ala
            660                 665                 670

Ala Leu Gly Leu Gly Ser Glu Asn Leu Tyr Phe Gln Gly Ser Gly Gly
            675                 680                 685

Gly Gly Glu Gln Lys Leu Ile Ser Glu Glu Asp Leu His His His His
            690                 695                 700

His His His His Pro Ser Thr Pro Pro Thr Pro Ser Pro Ser Thr Pro
705                 710                 715                 720

Pro Thr Pro Ser Pro Ser Tyr Lys Thr Gln Gly Lys Thr Glu Phe Cys
                725                 730                 735

Ala

<210> SEQ ID NO 11
<211> LENGTH: 405
<212> TYPE: PRT
<213> ORGANISM: Artificial Sequence
<220> FEATURE:
<223> OTHER INFORMATION: pYS6/CT* MFalpha1-scFv lysozyme-NorpA

<400> SEQUENCE: 11

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80
```

```
Ser Leu Glu Lys Arg Glu Ala Glu Ala Ala Ser Gln Val Lys Leu Gln
            85                  90                  95

Gln Ser Gly Ala Glu Leu Val Lys Pro Gly Ala Ser Val Lys Leu Ser
        100                 105                 110

Cys Thr Ala Ser Gly Phe Asn Ile Lys Asp Thr Tyr Met His Trp Val
        115                 120                 125

Lys Gln Arg Pro Glu Gln Gly Leu Glu Trp Ile Gly Arg Ile Asp Pro
        130                 135                 140

Ala Asn Gly Asn Thr Lys Tyr Asp Pro Lys Phe Gln Gly Lys Ala Thr
145                 150                 155                 160

Ile Thr Ala Asp Thr Ser Ser Asn Thr Ala Tyr Leu Gln Leu Ser Ser
                165                 170                 175

Leu Thr Ser Glu Asp Thr Ala Val Tyr Tyr Cys Ala Arg Trp Asp Trp
            180                 185                 190

Tyr Phe Asp Val Trp Gly Gln Gly Thr Thr Val Thr Val Ser Ser Gly
        195                 200                 205

Gly Gly Gly Ser Gly Gly Gly Ser Gly Gly Gly Ser Asp Ile
        210                 215                 220

Glu Leu Thr Gln Ser Pro Ser Ser Met Tyr Thr Ser Leu Gly Glu Arg
225                 230                 235                 240

Val Thr Ile Thr Cys Lys Ala Ser Gln Asp Ile Asn Ser Tyr Leu Arg
                245                 250                 255

Trp Phe Gln Gln Lys Pro Gly Lys Ser Pro Lys Thr Leu Ile Tyr Tyr
            260                 265                 270

Ala Thr Ser Leu Ala Asp Gly Val Pro Ser Arg Phe Ser Gly Ser Gly
        275                 280                 285

Ser Gly Gln Asp Tyr Ser Leu Thr Ile Ser Ser Leu Glu Ser Asp Asp
        290                 295                 300

Thr Thr Thr Tyr Tyr Cys Leu Gln His Gly Glu Ser Pro Tyr Thr Phe
305                 310                 315                 320

Gly Gly Gly Thr Lys Leu Glu Ile Lys Arg Ala Ala Ala Glu Gln Lys
                325                 330                 335

Leu Ile Ser Glu Glu Asp Leu Asn Gly Ser Glu Asn Leu Tyr Phe Gln
            340                 345                 350

Gly Ser Gly Gly Gly Gly Glu Gln Lys Leu Ile Ser Glu Glu Asp Leu
        355                 360                 365

His His His His His His His Pro Ser Thr Pro Pro Thr Pro Ser
        370                 375                 380

Pro Ser Thr Pro Pro Thr Pro Ser Pro Ser Tyr Lys Thr Gln Gly Lys
385                 390                 395                 400

Thr Glu Phe Cys Ala
            405

<210> SEQ ID NO 12
<211> LENGTH: 114
<212> TYPE: PRT
<213> ORGANISM: Artificial Sequence
<220> FEATURE:
<223> OTHER INFORMATION: pYD_NBC1_Aga2-NorpA

<400> SEQUENCE: 12

Met Gln Leu Leu Arg Cys Phe Ser Ile Phe Ser Val Ile Ala Ser Val
1               5                   10                  15

Leu Ala Gln Glu Leu Thr Thr Ile Cys Glu Gln Ile Pro Ser Pro Thr
            20                  25                  30
```

Leu Glu Ser Thr Pro Tyr Ser Leu Ser Thr Thr Ile Leu Ala Asn
          35                  40                  45

Gly Lys Ala Met Gln Gly Val Phe Glu Tyr Tyr Lys Ser Val Thr Phe
 50                  55                  60

Val Ser Asn Cys Gly Ser His Pro Ser Thr Thr Ser Lys Gly Ser Pro
 65                  70                  75                  80

Ile Asn Thr Gln Tyr Val Phe Lys Leu Leu Gln Ala Ser Gly Gly
                 85                  90                  95

Gly Ser Gly Gly Gly Gly Ser Tyr Lys Thr Gln Gly Lys Thr Glu Phe
            100                 105                 110

Cys Ala

<210> SEQ ID NO 13
<211> LENGTH: 327
<212> TYPE: PRT
<213> ORGANISM: Artificial Sequence
<220> FEATURE:
<223> OTHER INFORMATION: pYS6/CT* MFalpha1-InaD-Fn10

<400> SEQUENCE: 13

Met Arg Phe Pro Ser Ile Phe Thr Ala Val Leu Phe Ala Ala Ser Ser
 1               5                  10                  15

Ala Leu Ala Ala Pro Val Asn Thr Thr Thr Glu Asp Glu Thr Ala Gln
             20                  25                  30

Ile Pro Ala Glu Ala Val Ile Gly Tyr Ser Asp Leu Glu Gly Asp Phe
         35                  40                  45

Asp Val Ala Val Leu Pro Phe Ser Asn Ser Thr Asn Asn Gly Leu Leu
 50                  55                  60

Phe Ile Asn Thr Thr Ile Ala Ser Ile Ala Ala Lys Glu Glu Gly Val
 65                  70                  75                  80

Ser Leu Glu Lys Arg Glu Ala Glu Ala Ser Ala Gly Glu Leu Ile
             85                  90                  95

His Met Val Thr Leu Asp Lys Thr Gly Lys Lys Ser Phe Gly Ile Cys
            100                 105                 110

Ile Val Arg Gly Glu Val Lys Asp Ser Pro Asn Thr Lys Thr Thr Gly
            115                 120                 125

Ile Phe Ile Lys Gly Ile Val Pro Asp Ser Pro Ala His Leu Cys Gly
            130                 135                 140

Arg Leu Lys Val Gly Asp Arg Ile Leu Ser Leu Asn Gly Lys Asp Val
145                 150                 155                 160

Arg Asn Ser Thr Glu Gln Ala Val Ile Asp Leu Ile Lys Glu Ala Asp
                165                 170                 175

Phe Lys Ile Glu Leu Glu Ile Gln Thr Phe Asp Lys Ser Gly Gly Gly
            180                 185                 190

Gly Glu Gln Lys Leu Ile Ser Glu Glu Asp Leu His His His His
            195                 200                 205

His Pro Ser Thr Pro Pro Thr Pro Ser Pro Ser Thr Pro Pro Thr Pro
210                 215                 220

Ser Pro Glu Asn Leu Tyr Phe Gln Gly Val Ser Asp Val Pro Arg Asp
225                 230                 235                 240

Leu Glu Val Val Ala Ala Thr Pro Thr Ser Leu Leu Ile Ser Trp Asp
                245                 250                 255

Ala Pro Ala Val Thr Val Arg Tyr Tyr Arg Ile Thr Tyr Gly Glu Thr
            260                 265                 270

Gly Gly Asn Ser Pro Val Gln Glu Phe Thr Val Pro Gly Ser Lys Ser

-continued

```
                275                 280                 285
Thr Ala Thr Ile Ser Gly Leu Lys Pro Gly Val Asp Tyr Thr Ile Thr
    290                 295                 300

Val Tyr Ala Val Thr Gly Arg Gly Asp Ser Pro Ala Ser Ser Lys Pro
305                 310                 315                 320

Ile Ser Ile Asn Tyr Arg Thr
                325
```

YEAST DISPLAY SYSTEMS

FIELD

The present invention relates to the field of protein display libraries and library screening. More specifically, the present invention relates to the production of proteins for display on cell surfaces.

BACKGROUND

Protein binding domains can be predicted from sequence data, however re-designing proteins with improved or altered binding affinities often requires testing of a number of variants of the re-designed protein. Currently the best method for obtaining proteins with desired binding affinities is to generate and screen a protein library including such variants that can include rationally redesigned proteins, randomly altered proteins, or a combination thereof. Libraries of many types of protein, such as immunoglobulins and scaffold proteins and receptors or receptor ligands have successfully been constructed and screened for binding affinity.

There are many methods to screen libraries, but one of the most common methods is the phage display method, which comprises fusion of a protein library to the coat proteins of filamentous phage (e.g., Huse et al., '89; Clackson et al., '91; Marks et al., '92). Fusions are made most commonly to a minor coat protein, called the gene III protein (pIII), which is present in three to five copies at the tip of the phage. The fused library is then displayed on the surface of the viral particle. The page display library can then be screened against an immobilized target protein. However, one major drawback of this method is that target proteins that bind the library with very high affinity are not always identified because the conditions required to elute the bound phase usually denature the phage particle such that it becomes impossible to identify the protein of interest. Another draw back of phage display libraries is the requirement that the target protein be immobilized on a solid surface, which can lead to difficulties in determining the actual affinity of a target protein for the phage display protein. Furthermore, some proteins of interest require post-translational modifications, such as glycosylation, methylation, or disulfide binding, that cannot be achieved when expressed in a phage particle.

An alternative method for screening protein libraries is to display the library on the surface of bacterial cells. This method solves many of the drawbacks associated with phage display, but has its own problems. One problem with bacterial display is that the bacterial capsule can cause steric hindrance to proteins displayed on the bacterial surface. Also, bacteria do not contain the machinery to properly fold eukaryotic proteins, so the protein of interest may not always be expressed within the bacterium. Similar to the problem in phage, bacteria cannot provide post-translational modifications, like disulfide binding, to a eukaryotic protein.

Wittrup et al. (U.S. Pat. Nos. 6,699,658 and 6,696,251) have developed a method for a yeast cell display library. This is a two component system, wherein the first component involves expressing one subunit of the yeast mating adhesion protein, agglutinin, which is anchored to the yeast cell wall. The second component involves expressing a protein library fused to a second subunit of the agglutinin protein which forms high affinity disulfide bonds to the first agglutinin subunit. The protein library fused to the agglutinin is thus displayed on the surface of the cell. The library can then be screened. This method allows for the proper folding and post-translational modification of eukaryotic proteins.

Rakestraw et al. (PCT/US2008/003978) have developed a three component system for displaying a protein library on the surface of yeast cells. The first component involves expressing a protein library fused to a biotin-binding peptide, the second component involves modifying the yeast cell wall to express biotin, and the third component involves binding avidin to the biotin expressed on the cell surface. The fused protein library is then biotinylated and secreted from the yeast cell and binds to the avidin on the yeast cell surface, thus displaying the protein library on the surface of the yeast cell. One potential drawback of this system is that avidin non-specifically binds all biotin. Another potential drawback is that avidin contains four binding sites, which may cause steric hindrance thus preventing the biotinylated protein library from binding to the cell surface bound avidin. Similarly, the avidin molecule may bind the biotinylated protein library before binding the biotinylated yeast cell wall, thereby hindering the binding of the avidin to the yeast cell wall. Additionally, this method contains the added complication of having to biotinylate the protein library within the yeast cell. This necessary extra step requires further modification to the yeast cell. It is well established that the more modifications are made to a biological system, the less likely it is that the system will behave as designed. In addition, since avidin/streptavidin is multivalent, care must be taken to not cross-link the biotinylated cells. Finally, biotin/streptavidin and biotin/avidin are used in a number of commercially available labeling kits. Such kits would be difficult to use in such a biotin/avidin display system.

The prior art lacks a simple, efficient system capable of specifically binding a secreted protein library using an adapter molecule that binds to the protein library and to the surface of a eukaryotic cell through different binding moieties.

SUMMARY OF THE INVENTION

The present invention meets this need by providing methods and compositions as disclosed through out the specification. One aspect includes host cells with a cell surface molecule attached to the surface of the cell, an adapter molecule comprising a first binding site and a second binding site, and a display molecule comprising a modified polypeptide where the first binding site binds specifically to the cell surface molecule and cannot bind to the display molecule, the second binding site binds specifically to the display molecule and cannot bind to the cell surface molecule, and the adapter molecule is not a component of the modified polypeptide. In certain embodiments, the host cell has a plurality of display molecules. In other embodiments which may be combined with the preceding embodiments, the host cell surface molecule may be covalently linked to the first binding site. In other embodiments which may be combined with the preceding embodiments, the host cell surface molecule may be covalently linked to the first binding site through a disulfide bond. In other embodiments which may be combined with any of the preceding embodiments, the host cell surface molecule may include a first agglutinin which may be Aga1p. In other embodiments which may be combined with any of the preceding embodiments, the host cell surface molecule may be attached to the cell membrane via a GPI anchor. In other embodiments which may be combined with any of the preceding embodiments, wherein the first binding site comprises a second agglutinin which may be Aga2p. In other embodiments which may be combined with any of the preceding embodiments, the second binding site may be covalently linked to the display molecule. In other embodiments which may be combined with any of the preceding embodiments, the second binding site may be covalently linked to the display molecule through disulfide bonds. In other embodiments which may be combined with any of the preceding embodiments, the second binding site includes a PDZ domain which may be the PDZ domain of InaD which may have the amino acid sequence of SEQ ID NO: 8. In other embodiments which may be combined with any of the preceding embodiments, the display molecule includes a NorpA ligand which may be at the C-terminus which may have the amino acid sequence of SEQ ID NO: 9. In other embodiments which may be combined with any of the preceding embodiments except where the second binding site includes a PDZ domain or where the display molecule comprises a NorpA ligand, the display molecule includes a PDZ domain which may be the PDZ domain of InaD which may have the amino acid sequence of SEQ ID NO: 8. In other embodiments which may be combined with any of the preceding embodiments except where the second binding site includes a PDZ domain or where the display molecule comprises a NorpA ligand, the second binding site includes a NorpA ligand which may be at the C-terminus which may have the amino acid sequence of SEQ ID NO: 9. In other embodiments which may be combined with any of the preceding embodiments, wherein the modified polypeptide may be a scaffold protein, a signal transduction protein, an antibody, an immunoglobulin, an immunoadhesin, a receptor, a ligand, an oncoprotein, a transcription factor, or an enzyme. In other embodiments which may be combined with any of the preceding embodiments, display molecule may be a fibronectin polypeptide which may include an F10 polypeptide. In other embodiments which may be combined with any of the preceding embodiments, the display molecule includes a secretion signal peptide may be an MFalpha secretion signal sequence, a glucoamylase, an Aga2 secretion signal sequence, an Flo1p secretion signal sequence, an invertase secretion signal sequence, or an acid phosphatase secretion signal sequence. In other embodiments which may be combined with any of the preceding embodiments, the secretion signal peptide may be an MFalpha/HSA hybrid leader peptide. In other embodiments which may be combined with any of the preceding embodiments, expression of the display molecule is under the control of a first inducible promoter which may be an AOX 1 promoter, a Cup 1 promoter, or a Gal promoter. In other embodiments which may be combined with any of the preceding embodiments, the expression of the adapter molecule is under the control of a second inducible promoter which may be an AOX 1 promoter, a Cup 1 promoter, or a Gal promoter. In other embodiments which may be combined with any of the preceding embodiments, the host cell may be a yeast cell which may be *Pichia pastoris* or *Saccharomyces cerevisiae*.

Another aspect includes libraries of host cells which include least two host cells in accordance with the preceding aspect and any and all of its embodiments where each host cell includes a different modified polypeptide.

Yet another aspect includes methods for displaying a modified polypeptide which includes (a) providing a host cell comprising a cell surface molecule attached to the surface of the cell and a first nucleic acid encoding a display polypeptide comprising a modified polypeptide, (b) contacting the host cell with an adapter molecule comprising a first binding site and a second binding site under conditions wherein the first binding site binds to the cell surface molecule, and then (c) incubating the host cell under conditions wherein the host cell exports the display polypeptide outside the host cell under conditions wherein the second binding site binds to the display polypeptide, where the first binding site binds specifically to the cell surface molecule and cannot bind to the display molecule, the second binding site binds specifically to the display polypeptide and cannot bind to the cell surface molecule, and the adapter molecule is not a component of the modified polypeptide. In other embodiments, the host cell may display at least $10^2$, at least $10^3$, at least $10^4$, or at least $10^5$ modified polypeptides. In other embodiments which may be combined with the preceding embodiments, the host cell surface molecule may be covalently linked to the first binding site. In other embodiments which may be combined with the preceding embodiments, the host cell surface molecule may be covalently linked to the first binding site through a disulfide bond. In other embodiments which may be combined with any of the preceding embodiments, the host cell surface molecule may include a first agglutinin which may be Aga1p. In other embodiments which may be combined with any of the preceding embodiments, the host cell surface molecule may be attached to the cell membrane via a GPI anchor. In other embodiments which may be combined with any of the preceding embodiments, wherein the first binding site comprises a second agglutinin which may be Aga2p. In other embodiments which may be combined with any of the preceding embodiments, the second binding site may be covalently linked to the display molecule. In other embodiments which may be combined with any of the preceding embodiments, the second binding site may be covalently linked to the display molecule through disulfide bonds. In other embodiments which may be combined with any of the preceding embodiments, the second binding site includes a PDZ domain which may be the PDZ domain of InaD which may have the amino acid sequence of SEQ ID NO: 8. In other embodiments which may be combined with any of the preceding embodiments, the display molecule includes a NorpA ligand which may be at the C-terminus which may have the amino acid sequence of SEQ ID NO: 9. In other embodiments which may be combined with any of the preceding embodiments except where the second binding site includes a PDZ domain or where the display molecule comprises a NorpA ligand, the display molecule includes a PDZ domain which may be the PDZ domain of InaD which may have the amino acid sequence of SEQ ID NO: 8. In other embodiments which may be combined with any of the preceding embodiments except where the second binding site includes a PDZ domain or where the display molecule comprises a NorpA ligand, the second binding site includes a NorpA ligand which may be at the C-terminus which may have the amino acid sequence of SEQ ID NO: 9. In other embodiments which may be combined with any of the preceding embodiments, wherein the modified polypeptide may be a scaffold protein, a signal transduction protein, an antibody, an immunoglobulin, an immunoadhesin, a receptor, a ligand, an oncoprotein, a transcription factor, or an enzyme. In other embodiments which may be combined with any of the preceding embodiments, display molecule may be a fibronectin polypeptide which may include an F10 polypeptide. In other embodiments which may be combined with any of the preceding embodiments, the display molecule includes a secretion signal peptide may be an MFalpha secretion signal sequence, a glucoamylase, an Aga2 secretion signal sequence, an Flo1p secretion signal sequence, an invertase secretion signal sequence, or an acid phosphatase secretion signal sequence. In other embodiments which may be combined with any of the preceding embodiments, the secretion signal peptide may be an MFalpha/HSA hybrid leader peptide. In other embodiments which may be combined with any of the preceding embodiments expression of the display molecule is under the control of a first inducible promoter which may be an AOX 1 promoter, a Cup 1 promoter, or a Gal promoter. In other embodiments which may be combined with any of the preceding embodiments, the expression of the adapter molecule is under the control of a second inducible promoter which may be an AOX 1 promoter, a Cup 1 promoter, or a Gal promoter. In other embodiments which may be combined with any of the preceding embodiments, the host cell may be a yeast cell which may be *Pichia pastoris* or *Saccharomyces cerevisiae*.

Still another aspect includes methods for generating a host cell display library which includes introducing into a plurality of host cells a display library of first nucleic acids each encoding a display polypeptide comprising a modified polypeptide, wherein at least two of the introduced first nucleic acids encode different modified polypeptides, wherein each host cell comprises a second nucleic acid which encodes a cell surface polypeptide and a third nucleic acid which encodes an adapter molecule comprising a first binding site and a second binding site, where the first binding site binds to the cell surface molecule but not the display polypeptide, the second binding site binds to the display polypeptide but not the cell surface molecule, and the adapter molecule is not a component of the modified polypeptide. This aspect may be combined with any of the embodiments of the preceding aspects.

The foregoing are non-limiting examples of the present invention. Additional aspects and embodiments may be found throughout the specification.

BRIEF DESCRIPTION OF THE DRAWINGS

FIG. 9A is the a control with unstained yeast cells; FIG. 9B are uninduced yeast cells expressing fibronectin; FIG. 9C are induced yeast cells expressing fibronectin showing a shift in the curve; FIG. 9D are uninduced yeast cells expressing HSA; and FIG. 9E are induced yeast cells expressing HSA showing a shift in the curve.

FIG. 10A is the a control with unstained yeast cells; FIG. 10B are uninduced yeast cells expressing fibronectin; FIG. 10C are induced yeast cells expressing fibronectin appearing as white spots; FIG. 10D are uninduced yeast cells expressing HISA; and FIG. 10E are induced yeast cells expressing HSA appearing as white spots.

DETAILED DESCRIPTION OF THE INVENTION

Definitions

Figure 1:
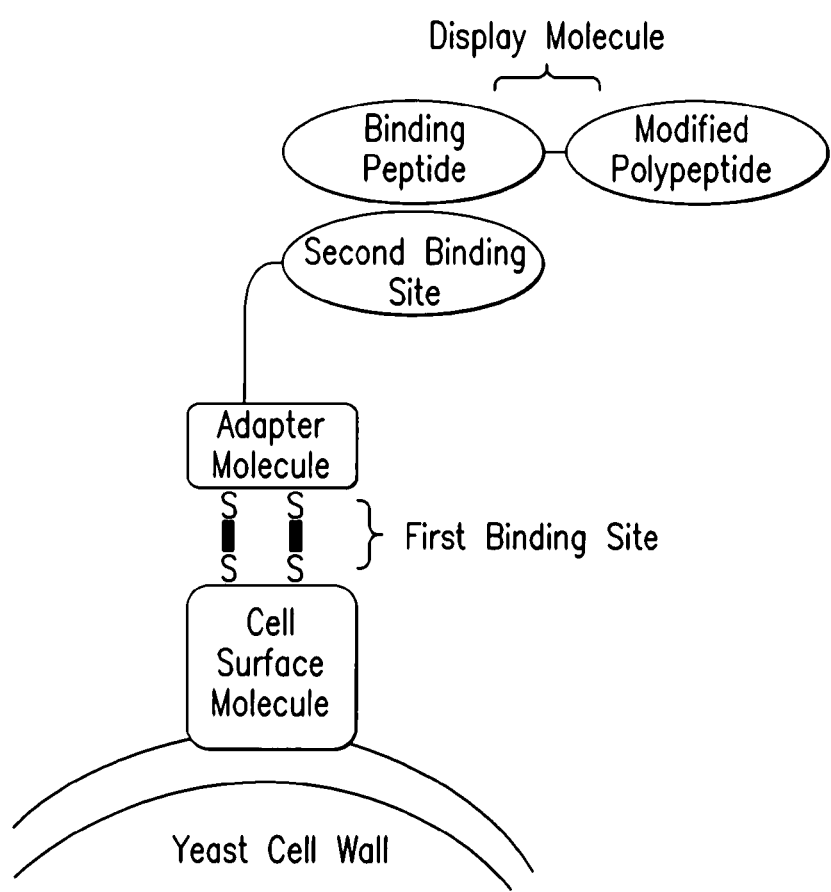
FIG. 1 shows a schematic of the three component system including the cell surface molecule, the adapter molecule including the first and second binding sites and the display molecule with the binding partner for the second binding site (a binding polypeptide in this embodiment) and a modified polypeptide as the molecule being displayed. In this embodiment, the host cell is a yeast cell.

As used herein the term "host cell" refers to a eukaryotic cell that has been modified to express a cell surface molecule, an adapter molecule, and a display molecule. Furthermore, it should be understood that the host cell secretes or excretes the display molecule prior to binding the display molecule to the adapter molecule on the surface of the host cell.

As used herein the term "cell surface molecule" refers to a peptide, polypeptide, binding domain, ligand, lipid, or carbohydrate that is directed to the extracellular surface of the host cell. The cell surface molecule may be anchored to the cell surface by covalent binding or non-covalent binding. The cell surface molecule may include a phospholipid, carbohydrate, or protein through which it attaches to the surface of the host cell. The cell surface molecule may be a polypeptide that binds to, or is conjugated to, a phospholipid, carbohydrate, or a polypeptide on the surface of the cell. For example, the polypeptide may use a phosphatidyl-inositol-glycan (GPI) anchor to attach to the surface of the host cell, such as a-agglutinins, α-agglutinins, and flocculins. The cell surface molecule may also be a transmembrane protein with a binding domain located on the surface of the host cell that can bind to the first binding site of the adapter molecule.

As used herein the term "adapter molecule" refers to a peptide, polypeptide, binding domain, ligand, lipid, or carbohydrate or combination of the foregoing that has two distinct binding sites. The adapter molecule has a binding site that specifically binds the cell surface molecule and a second distinct binding site that specifically binds the display molecule. Without limiting the invention, the two binding sites of the polypeptide may be polypeptide domains each with its own binding affinity to a different molecule that are fused together. For example, the polypeptide may be an a-agglutinin subunit, such as Aga2p, fused to a PDZ domain, or it may be a flocculin, such as Flo1, fused to a PDZ domain.

As used herein the term "first binding site" refers to a region of the adapter molecule that specifically recognizes and binds at least a portion of the cell surface molecule. For example, the first binding site may comprise a peptide, polypeptide, binding domain, ligand, lipid, or carbohydrate or combination thereof that specifically binds to a cell surface molecule which could include, without limitation, a peptide, binding domain, ligand, protein, lipoprotein, lipid, or carbohydrate. More specifically, but without limiting the invention, the first binding site may refer to the Aga2p subunit of a-agglutinin that specifically binds to the Aga1p subunit of a-agglutinin through disulfide bonds. In general, any two molecular binding partners may be used for the first binding site and the corresponding portion of the cell surface molecule. Examples include $Ni^{2+}$ ions and polyhistidine tags, sugar residues and Concanavalin A, p-aminophenyl-β-D-thiogalactoside and β-galactosidase (Germino et al., Proc. Natl. Acad. Sci. USA 80:6848 (1983), glutathione and glutathione-S-transferase (Smith, D. B. and Johnson, K. S. Gene 67:31 (1988)); staphylococcal protein A and IgG (Uhlen, M. et al. Gene 23:369 (1983)), calmodulin nickel binding proteins (CNBP) and calmodulin agarose (Stofko-Hahn, R. E. et al. FEBS Lett. 302(3):274-278); streptavidin or avidin and biotin (Takashige. S. and Dale, G. L., Proc. Natl. Acad. Sci. USA. 85:1647-1651 (1988)); amylase and maltose-binding protein domain from the malE gene of *E. coli* (Bach, H. et al., J. Mol. Biol. 312:79-93 (2001)), any epitope and its corresponding antibody (See, Kolodziej, P. A. and Young, R. A., Methods Enzymol. 194:508-519 (1991), e.g., the FLAG™ octapeptide or antidigoxygenin antibody and digoxygenin).

As used herein the term "second binding site" refers to a region of the adapter molecule that specifically recognizes and binds the display molecule. For example, the second binding site may comprise a peptide, polypeptide, binding domain, ligand, lipid, or carbohydrate that specifically binds to a peptide, ligand, protein, lipoprotein, lipid, or carbohydrate comprising the display molecule. More specifically, but without limitations, the second binding site may refer to a PMZ domain that specifically binds to a NorpA ligand. Any of the binding pairs suitable for the first binding site may also be used for the second binding site so long as they do not recognize the same partners.

As used herein the term "display molecule" refers to a molecule that can be localized to the surface of the host cell via binding of the adapter molecule on the surface of the host cell. The display molecule will typically comprise the molecule (or library of molecules) to be displayed and a binding partner that is specifically bound by the second binding site of the adapter molecule. In certain instances the molecule to be displayed and the binding partner may be one in the same. By way of example, the display molecule may comprise a peptide, polypeptide, binding domain, ligand, lipid, or carbohydrate or combination thereof. It should be understood that the display molecule is expressed or otherwise generated within the host cell and is secreted or excreted out of the cell so as to be displayed on the surface of said cell. The display molecule may comprise a library of varied molecules that can be screened for binding to a target or for improved or altered activity. In certain embodiments, the library may comprise modified polypeptides. The display molecule may also comprise a tag or peptide that can be labeled so as to detect binding of the display molecule to the cell surface, or sort host cells displaying said molecule.

As used herein the term "modified polypeptide" refers to any polypeptide of interest that is fused to a peptide, polypeptide, binding domain, ligand, lipid, or carbohydrate that specifically binds to a peptide, ligand, protein, lipoprotein, lipid, or carbohydrate comprising the second binding site of the adapter molecule, and is displayed on the surface of the host cell (and is therefore a component of the display molecule). Non-limiting examples of the modified polypeptide are scaffold proteins, signal transduction proteins, antibodies, immunoglobulins, immunoadhesins, receptors, ligands, oncoproteins, transcription factors, and enzymes.

As used herein, the term "plurality of display molecules" refers to at least two copies of the display molecule displayed on the surface of host cells. In certain instances, each unique display molecule is displayed by a different host cell.

As used herein the term "component of the modified polypeptide" refers to any naturally occurring binding partners of any fragment of the modified peptide. Non-limiting examples include an immunoglobulin light chain binding to an immunoglobulin heavy, a biotin molecule binding avidin, two subunits of α-hemoglobin dimerizing, a myosin heavy chain binding to a myosin light chain, two monomers of glycophorin A dimerizing, or two monomers of any naturally occurring dimer protein binding to one another.

As used herein the term "library of host cells" refers to a plurality of host cells, wherein each host cell comprises a non-identical modified polypeptide that is displayed on the surface of the cell.

As used herein the term "non-identical modified polypeptide" refers to the amino acid sequence of at least two modified polypeptides, wherein each amino acid sequence comprises amino acid substitutions, insertions, or deletions which differentiate one modified polypeptide displayed on the surface of a host cell from another modified polypeptide displayed on the surface of a second host cell.

As used herein the term "Fn10" refers to the tenth type III domain of human fibronectin.

Display Molecules

The display molecules may be used to display any molecule that may be expressed or otherwise generated in a host cell. Non limiting examples of such molecules follow.

Antibody Scaffold

The display molecules may be immunoglobulins. Methods of generating libraries of immunoglobulins were initially developed to display the immunoglobulins via phage, but additional methods of display have since been developed. All of the methods of generating libraries for these alternative methods of display may be adapted to allow display using the methods disclosed herein. Exemplary method of generating libraries of antibodies may be found in: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Non-Antibody Scaffold

Known non-immunoglobulin frameworks or scaffolds which may be displayed using the methods disclosed herein include, but are not limited to, fibronectins (Compound Therapeutics, Inc., Waltham, Mass.), ankyrin (Molecular Partners AG, Zurich, Switzerland), domain antibodies (Domantis, Ltd (Cambridge, Mass.) and Ablynx nv (Zwijnaarde, Belgium)), lipocalin (Anticalin) (Pieris Proteolab AG, Freising, Germany), small modular immuno-pharmaceuticals (Trubion Pharmaceuticals Inc., Seattle, Wash.), maxybodies (Avidia, Inc. (Mountain View, Calif.)), Protein A (Affibody AG, Sweden) and affilin (gamma-crystallin or ubiquitin) (Scil Proteins GmbH, Halle, Germany), protein epitope mimetics (Polyphor Ltd, Allschwil, Switzerland).

(i) Fibronectins

The adnectin scaffolds are based on fibronectin type III domain (e.g., the tenth module of the fibronectin type III (10 Fn3 domain). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands. (U.S. Pat. No. 6,673,901).

These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin fibronectin molecule mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the disclosure using standard cloning techniques.

(ii) Ankyrin—Molecular Partners

The technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

(iii) Maxybodies/Avimers—Avidia

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, 20040175756; 20050053973; 20050048512; and 20060008844.

(vi) Protein A—Affibody

Affibody® affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate Affibody® libraries with a large number of ligand variants (See e.g., U.S. Pat. No. 5,831,012). Affibody® molecules mimic antibodies, they have a molecular weight of 6 kDa, compared to the molecular weight of antibodies, which is 150 kDa. In spite of its small size, the binding site of Affibody® molecules is similar to that of an antibody.

(v) Anticalins—Pieris

Anticalins® are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids.

The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain.

The set of four loops, which makes up the binding pocket, shows pronounced structural plasticity and tolerates a variety of side chains. The binding site can thus be reshaped in a proprietary process in order to recognize prescribed target molecules of different shape with high affinity and specificity.

One protein of lipocalin family, the bilin-binding protein (BBP) of Pieris Brassicae has been used to develop anticalins by mutagenizing the set of four loops. One example of a patent application describing "anticalins" is PCT WO 199916873.

(vi) Affilin—Scil Proteins

Affilin™ molecules are small non-immunoglobulin proteins which are designed for specific affinities towards proteins and small molecules. New Affilin™ molecules can be very quickly selected from two libraries, each of which is based on a different human derived scaffold protein.

Affilin™ molecules do not show any structural homology to immunoglobulin proteins. Scil Proteins employs two Affilin™ scaffolds, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368.

(vii) Protein Epitope Mimetics (PEM)

PEM are medium-sized, cyclic, peptide-like molecules (MW 1-2 kDa) mimicking beta-hairpin secondary structures of proteins, the major secondary structure involved in protein-protein interactions.

Non-Scaffold

In addition to scaffolds which are useful for de novo generation of molecule with specific affinity, the methods disclosed herein may be used to display any other biological molecule that can be expressed or otherwise generated in the host cell. Libraries of such biological molecules, particularly polypeptides which can be encoded by polynucleotides for easy expression by the host cell, may be screened for improved characteristics of interest such as improved binding between receptor and ligand where the receptor or the ligand are part of the display molecule or improved enzymatic activity where the enzyme is part of the display molecule.

Expression Systems

Expression vectors may be used to express one or more of the cell surface molecules, the adapter molecule and the display molecule, in the host cell. Expression vectors for eukaryotic host cells typically include (i) eukaryotic DNA elements that control initiation of transcription, such as a promoter, (ii) eukaryotic DNA elements that control the processing of transcripts, such as a transcription termination/polyadenylation signal sequence, and (iii) optionally, eukaryotic DNA elements that control replication in the eukaryotic host cell if the vector is to be independently replicated (e.g., non-integrating vectors). To ease construction of such expression vectors, the vectors may optionally include (iv) prokaryotic DNA elements coding for a bacterial replication origin and an antibiotic resistance marker to provide for the growth and selection of the expression vector when manipulating the vector in the bacterial host cell. Appropriate eukaryotic expression vectors for use with fungal, yeast, and mammalian cellular hosts are known in the art, and are described in, for example, Powels et al. (Cloning Vectors: A Laboratory Manual, Elsevier, N.Y., 1985).

Yeast host cells are of particular interest and include *Saccharomyces cerevisiae, Pichia pastoris*, and *Pichia methanolica*. These vectors include YIp-based vectors, such as YIp5, YRp vectors, such as YRp17, YEp vectors such as YEp13 and YCp vectors, such as YCp19. A number of vectors exist for the expression of recombinant proteins in yeast. Other example of the YEp vectors include YEp24, YEp51, and YEp52, which are cloning and expression vehicles useful in the introduction of genetic constructs into *S. cerevisiae* (see, e.g., Broach et al. (1983) in Experimental Manipulation of Gene Expression, ed. M. Inouye Academic Press, p. 83). These vectors are also shuttle vectors in that they can replicate in *E. coli* due the presence of the pBR322 ori, and in *S. cerevisiae* due to the replication determinant of the yeast 2 micron plasmid.

Suitable promoters for function in yeast include the promoters for metallothionein, 3-phosphoglycerate kinase (Hitzeman et al., J. Biol. Chem. 255, 2073 (1980) or other glycolytic enzymes (Hess et al., J. Adv. Enzyme Req. 7, 149 (1968); and Holland et al. Biochemistry 17, 4900 (1978)), such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phospho-glucose isomerase, and glucokinase. Suitable vectors and promoters for use in yeast expression are further described in R. Hitzeman et al., EP073,657. Other suitable promoters for expression in yeast include the promoters from GAL1 (galactose), PGK (phosphoglycerate kinase), ADH (alcohol dehydrogenase), AOX1 (alcohol oxidase), HIS4 (histidinol dehydrogenase), and the like. Many yeast cloning vectors readily available and can be modified following the above discussion. Still other promoters, which have the additional advantage of transcription controlled by growth conditions, are the promoter regions for alcohol dehydrogenase 2, isocytochrone C, acid phosphatase, degradative enzymes associated with nitrogen metabolism, and the afore-mentioned metallothioncin and glyceraldehyde-3-phosphate dehydrogenase, as well as enzymes responsible for maltose and galactose utilization. Finally, promoters that are active in only one of the two haploid mating types may be appropriate in certain circumstances. Among these haploid-specific promoters, the pheromone promoters MFa1 and MFα1 are of particular interest.

Secretion from yeast host cells of the components including the adapter molecule (if produced in the host cell) and the display molecule may be increased by use any available secretion signal sequences of yeast proteins. One example is the leader sequence of a precursor of yeast mating pheromone, α-factor, which has also been used to direct secretion of heterologous proteins in yeast (See, e.g., Valenzuela, P., eds pp. 269-280, Butterworths, London; Brake, A. J. (1990) Meth. Enzymol. 185, 408-441). The α-factor leader sequence, in addition to the N-terminal signal peptide of 17 residues, includes a hydrophilic pro-region which contains 72 residues and bears three sites of N-linked glycosylation. The pro-region is extensively glycosylated in the ER and Golgi and is cleaved by Kex2 endopeptidase in the late Golgi compartment. The presence of the pro-region at the N-terminus is believed to allow some heterologous proteins to pass the quality control in the ER and to reach the periplasm.

Another example is the leader sequence from yeast invertase (MLLQAFLFLLAGFAAKISADAHKS) (SEQ ID NO: 1). This leader sequence has been demonstrated to be cleaved from nascent heterologous peptide upon entrance into the endoplasmic reticulum. The enzyme responsible for cleavage of the pre sequence, Kex2, resides in the trans Golgi. A further example is the signal sequence of yeast acid phosphatase which may be used to direct the secretion of the components disclosed herein.

Methods for transforming *S. cerevisiae* cells with exogenous DNA and producing recombinant polypeptides therefrom are disclosed by, for example, Kawasaki, U.S. Pat. No. 4,599,311, Kawasaki et al., U.S. Pat. No. 4,931,373, Brake, U.S. Pat. No. 4,870,008, Welch et al., U.S. Pat. No. 5,037,743, and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media.

Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., J. Gen. Microbiol. 132:3459 (1986), and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Laambowitz, U.S. Pat. No. 4,486,533.

For example, the use of *Pichia methanolica* as host for the production of recombinant proteins is disclosed by Raymond, U.S. Pat. No. 5,716,808, Raymond, U.S. Pat. No. 5,736,383, Raymond et al., Yeast 14:11-23 (1998), and in international publication Nos. WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. *P. methanolica* cells can be transformed by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

For use of mammalian host cells, mammalian expression vectors are also well known in the art and may be used as well. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL. 8544, ATCC CRL 10314), canine kidney cells (MDCK; ATCC CCL 34), Chinese hamster ovary cells (CHO-K1; ATCC CCL61; CHO DG44 (Chasin et al., Som. Cell. Molec. Genet. 12:555, 1986)), rat pituitary cells (GH1; ATCC CCL82), HeLa S3 cells (ATCC CCL2.2), rat hepatoma cells (H4-II-E; ATCC CRL 1548) SV40-transformed monkey kidney cells (COS-1; ATCC CRL 1650) and murine embryonic cells (NIH-3T3; ATCC CRL 1658).

EXAMPLES

The following provides non-limiting examples of the systems, compositions and methods disclosed herein. Proteins can be displayed on the surface of yeast cells by utilizing the PDZ domain of the yeast InaD protein and the C-terminal 5 amino acids of the yeast NorpA protein. This three component protein display system consists of a vector expressing the protein to be displayed with a secretion signal fused at its N-terminus, and the NorpA ligand fused at the C-terminus; a second vector expressing an adapter protein that can bind specifically to a yeast cell wall protein, and which is fused to the PDZ domain of InaD, which binds specifically to the NorpA ligand; and a third vector that express a yeast cell wall protein that binds specifically to the adapter protein. This system has been adapted for use in *Saccharomyces cerevisiae* and *Pichia pastoris*.

Example 1

Yeast Display Using InaD/NorpA Interaction it *Pichia pastoris*

The protein display system for *P. pastoris* was developed to display a fibronectin type III domain (Fn10), by fusing a hybrid secretion sequence (MFalpha/HSA) or a yeast leader sequence (MFalpha1) at N-terminus of Fn10 and fusing the NorpA ligand to its C-terminus. Once expressed, the Fn10 was secreted from the cell and the NorpA ligand bound specifically to the PDZ domain of InaD through disulfide bonds. The InaD was fused to the C-terminus of the Agap2 protein. The Aga2p-InaD fusion protein served as the adapter protein, and the N-terminal Aga2p bound Aga1p, which was immobilized on the surface of the cell. Aga2p bound specifically to Aga1p through disulfide bonds.

The three component system consisting of the Fn10-NorpA fusion protein, the Aga2p-InaD fusion protein, and the Aga1p cell surface protein were cloned into pPIC expression vectors, under the control of an inducible promoter. The inducible promoter used was the AOX1 promoter, which is induced by methanol. Thus when methanol was added to yeast cells transformed with the vectors, the three proteins were expressed. Aga1p was expressed on the surface of the cell. Aga2p-InaD was localized to the cell surface where the N-terminal region of Aga2p-InaD bound to Aga1p. Fn10-NorpA was localized to the secretory pathway, was secreted from the cell, and bound InaD via the C-terminal NorpA ligand (FIG. 1). The system can also be switched such that the InaD is fused to Aga1 and NorpA is fused to Aga2p (See FIGS. 12 and 13).

A c-myc epitope tag was fused between the NorpA ligand and the C-terminus of Fn10. The c-myc epitope allowed for the detection of the displayed fibronectin by using a c-myc antibody. The fluorescently labeled c-myc antibody bound to the c-myc epitope on the surface of the cell was detected by fluorescence-activated cell sorting (FACS).

Strains and Media

The *Escherichia coli* Top10 strain (Invitrogen Carlsbad, Calif.) was used as the host strain for recombinant DNA manipulation. The *P. pastoris* GS115 strain (Invitrogen Co., Carlsbad, Calif.) was used for the production of the fusion protein AGA2-InaD and HSA/MFalpha1-Fn10-NorpA. *E. coli* was cultivated in LB medium (1% tryptone, 0.5% yeast extract, and 0.5% sodium chloride) containing 100 ug/mL ampicillin. *P. pastoris* was cultivated in BMGY medium (1% yeast extract, 2% peptone, 100 mM potassium phosphate buffer (pH 6.0), 1.34% yeast nitrogen base, $4 \times 10^{-5}$% biotin, and 1% glycerol), and BMMY medium (1% yeast extract, 2% peptone, 100 mM potassium phosphate buffer (pH 6.0), 1.34% yeast nitrogen base, $4 \times 10^{-5}$% biotin, and 0.5-2.0% methanol).

Construction of Expression Plasmids

Figure 2:
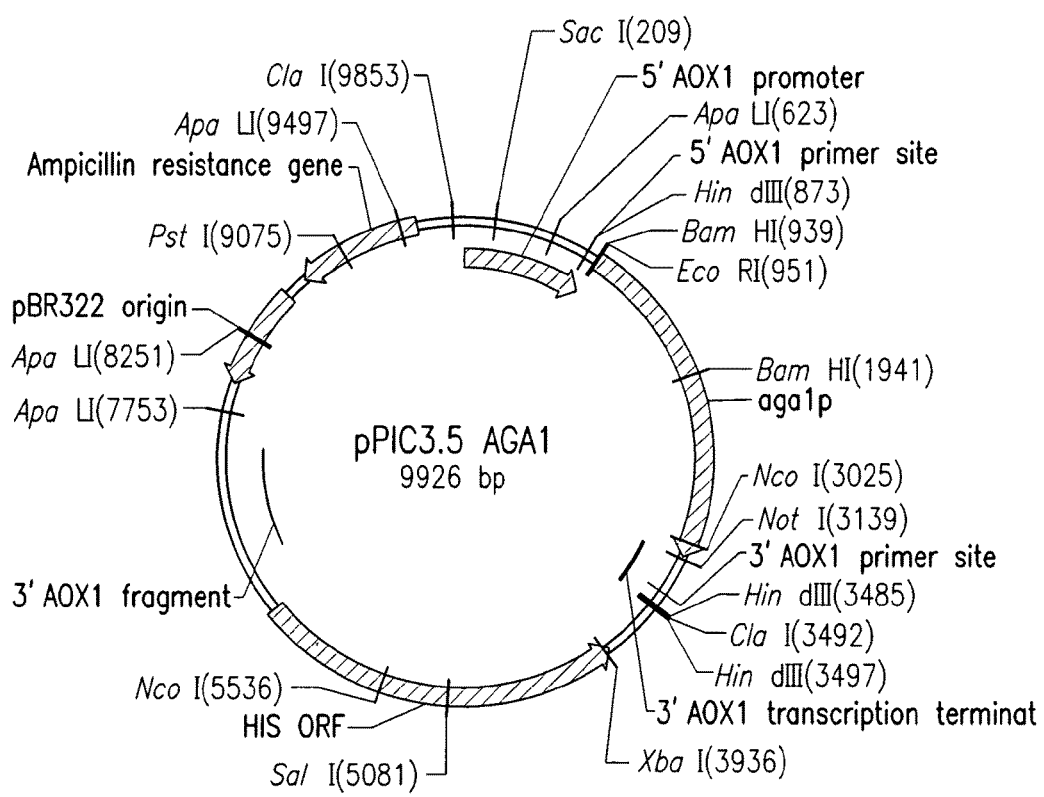
FIG. 2 shows the pPIC3.5 AGA1 vector for yeast expression of the Aga1p as the cell surface molecule.
Figure 3:
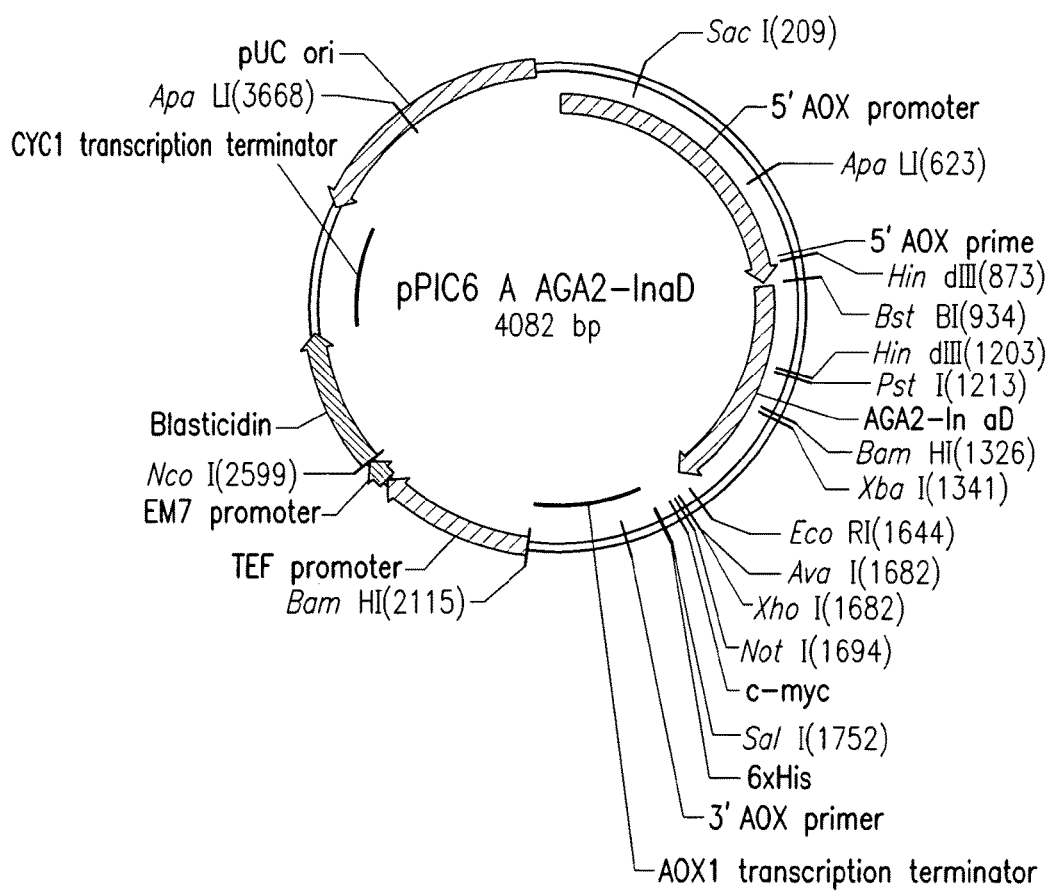
FIG. 3 shows the pPIC6 A AGA2-InaD vector for yeast expression of the Aga2p-InaD fusion polypeptide as the adapter molecule.
Figure 4:
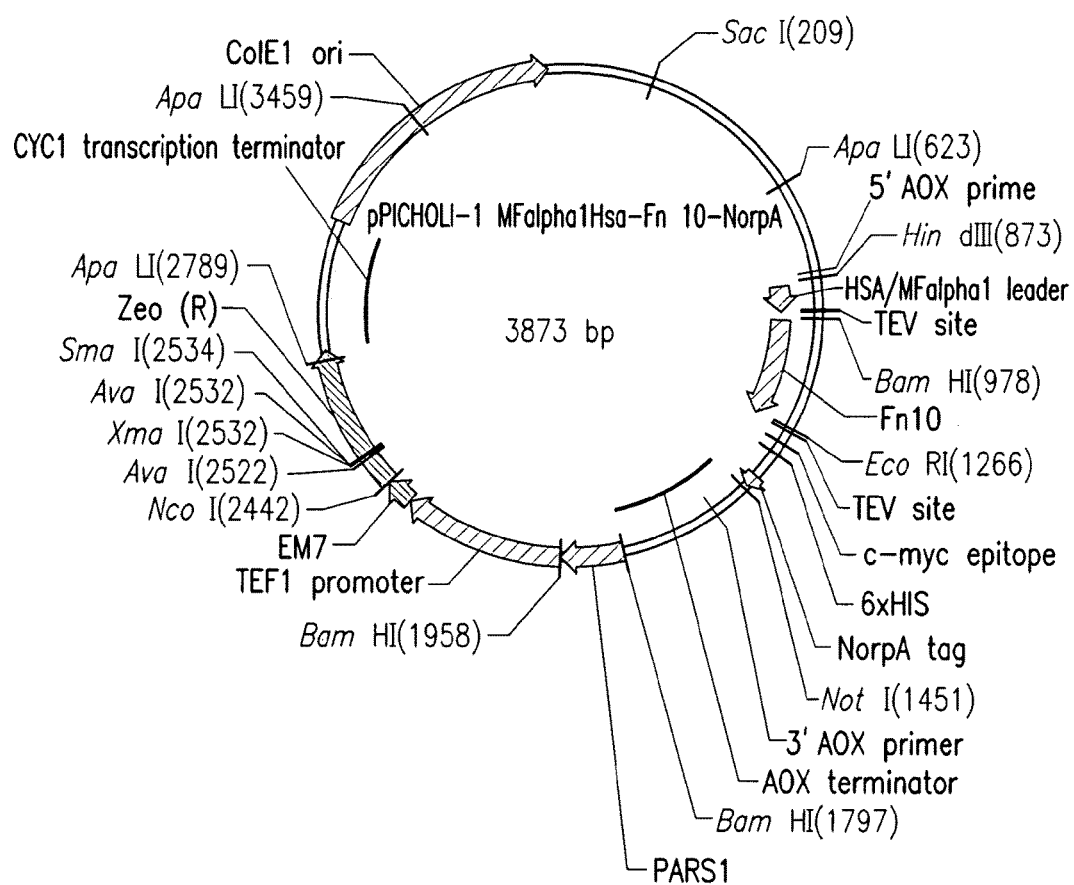
FIG. 4 shows the pPICHOLI-1 MFalpha1Hsa-Fn10-NorpA vector for yeast expression of the MFalpha1Hsa-Fn10-NorpA fusion polypeptide as the display molecule where the NorpA is the binding partner of the second binding site of the adapter molecule (i.e., InaD) and the fibronectin F10 domain is modified polypeptide.
Figure 5:
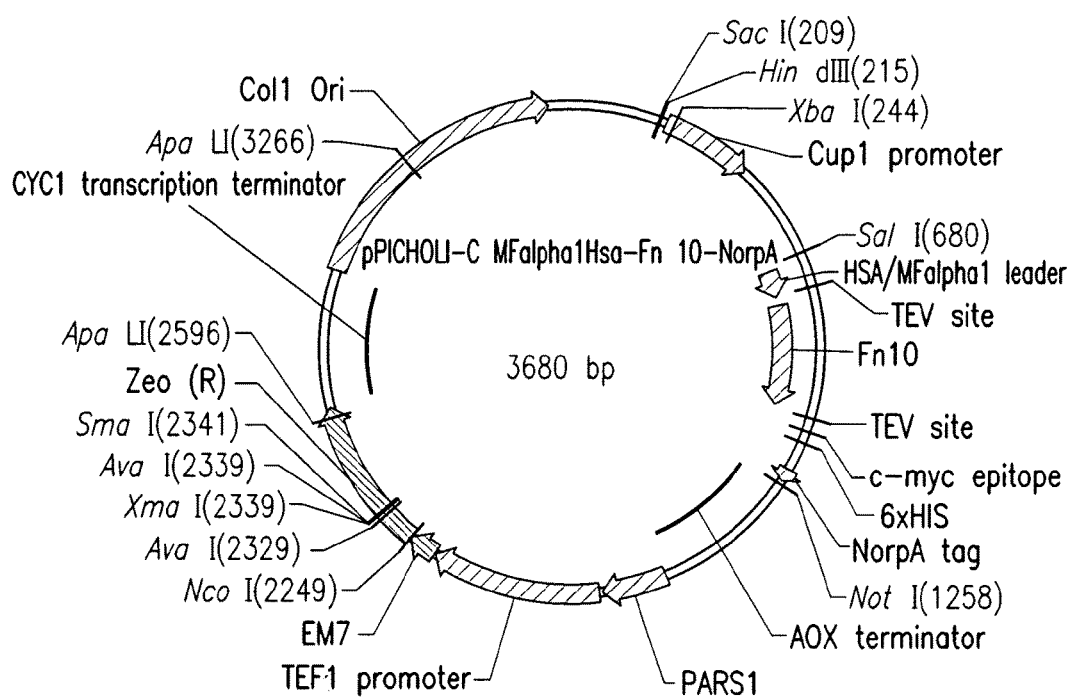
FIG. 5 shows the pPICHOLI-C MFalpha1Hsa-Fn10-NorpA vector for yeast expression of the MFalpha1Hsa-Fn10-NorpA fusion polypeptide as the display molecule where the NorpA is the binding partner of the second binding site of the adapter molecule (i.e., InaD) and the fibronectin F10 domain is modified polypeptide.
Figure 6:
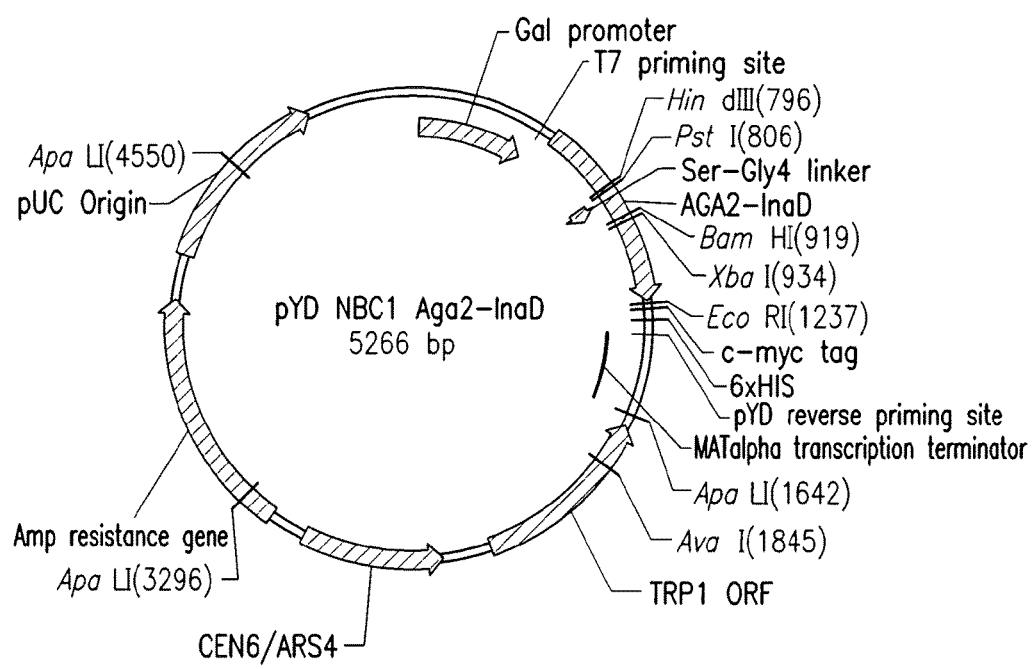
FIG. 6 shows the pYD NBC1 Aga2-InaD vector for yeast expression of the Aga2p-InaD fusion polypeptide as the adapter molecule.
Figure 7:
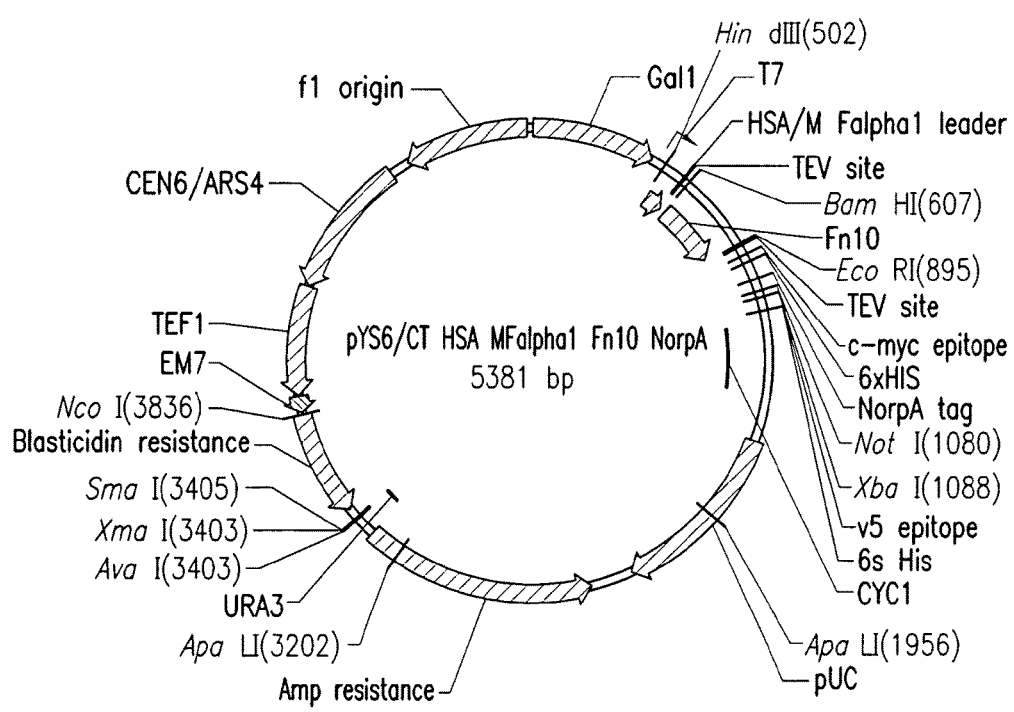
FIG. 7 shows the pYS HISA MFalpha1 Fn10 NorpA vector for yeast expression of the MFalpha1HSA-Fn10-NorpA fusion polypeptide as the display molecule where the NorpA is the binding partner of the second binding site of the adapter molecule (i.e., InaD) and the fibronectin F0 domain is modified polypeptide.

The gene corresponding to AGA1 was synthesized by Geneart and subcloned into pPIC3.5 (Invitrogen). The resulting vector was named pPIC3.5-AGA1 (FIG. 2). The AGA2-InaD anchor gene was synthesized by Geneart (Germany) and subcloned into expression vector pPIC6a (Invitrogen) using Bst1 and EcoR1 restriction sites. The resulting vector was named pPIC6-AGA2-InaD (FIG. 4). The fibronectin construct consists of the MFalpha1/HSA hybrid leader followed by the fibronectin fused at the C-terminus to the NorpA ligand sequence. The complete gene was synthesized by Geneart (Germany) and subcloned into pPICHOLI-1 (Mobitec). The resulting vector was named pPICHOLI-1 MFalpha1Hsa-Fn10-NorpA (FIG. 6).

Yeast Transformation.

Electro-competent *P. pastoris* GS115 (Invitrogen) strain was prepared according to the protocol specified by the supplier and co-transformed with Sail-digested pPIC3.5-AGA1, pPIC6-AGA2-InaD, and pPICHOLI-1 MFalpha1Hsa-Fn10-NorpA.

Cultivation Conditions

The yeast transformants were precultivated in BMGY medium containing 100 ug/ml Zeocin and 200 ug/ml Blasticidin at 30° C. for 16 hr. and used to inoculate 200 ml of BMGY medium (containing 100 ug/ml Zeocin and 200 ug/ml Balsticidin) in a 1 l baffle flask to give an initial $OD_{600}$ value of 0.1. After 24 hr. of cultivation, the culture was centrifuged at 1000 g for 10 min. and resuspended in BMMY medium (+100 ug/ml Zeocin and 200 ug/ml Blasticidin) containing 0.5%, 1.0%, or 2.0% methanol. To maintain the induction of the fusion proteins, 100% methanol was added every 24 hr. to the culture to the final concentrations mentioned above. Analysis of displayed fibronectins on the surface of yeast is performed using FACS and anti-myc antibody.

Example 2: Switch System to Secrete or Display Fibronectins on the Surface of *Pichia pastoris*

Figure 8:
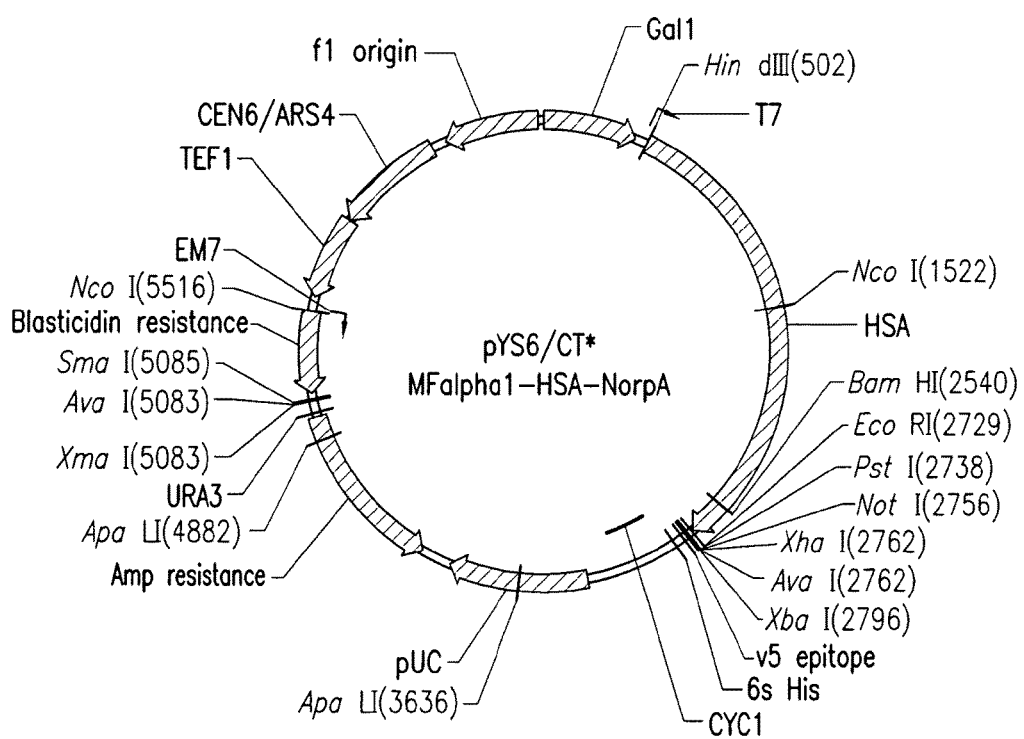
FIG. 8 shows the pYS MFalpha1 HSA NorpA vector for yeast expression of the MFalpha1HSA- -NorpA fusion polypeptide as the display molecule where the NorpA is the binding partner of the second binding site of the adapter molecule (i.e., InaD) and the HSA is the displayed polypeptide.

One variant of the above display system enables the choice between secretion and display of proteins from *P. pastoris*. To achieve this, the fibronectin construct consisting of the MFalpha1/HSA hybrid leader followed by fibronectin fused at the C-terminus to the NorpA ligand sequence is cloned into pPICHOLI-C instead of pPICHOLI-1. The resulting vector is named pPICHOLI-C MfalphalHsa-Fn10-NorpA (FIG. 8). The key difference between the two vectors is the promoter, which in pPICHOLI-1 is the AOX1 promoter induced by methanol, and in the pPICHOLI-C is the Cup1 promoter induced by copper. To display the fibronectin on the surface of *P. pastoris*. AGA1 and AGA2-InaD are induced with methanol, while pPICHOLI-C is induced with copper. This allows for the capture of the secreted fibronectin on the surface of yeast mediated through the tight InaD/NorpA interaction. For secretion of the fibronectin without displaying the protein on the surface of yeast, induction with copper is sufficient. Without the induction of AGA1 and AGA2-InaD (driven by methanol) the binding partner for NorpA (AGA1/AGA2-InaD) is not present on the surface of yeast and therefore the fibronectin will be secreted.

Example 3: Yeast Display Using InaD/NorpA Interaction in *Saccharomyces cerevisiae*

Figure 12:
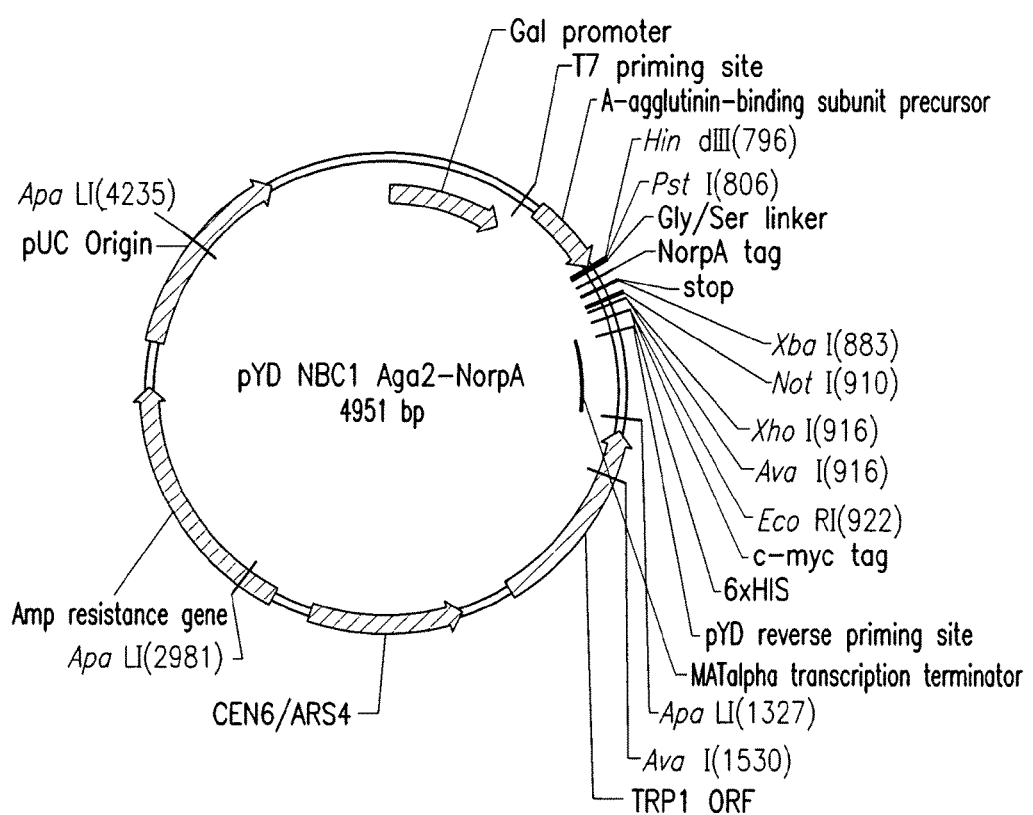
FIG. 12 shows a reversed system in which the pYD NBC1 Aga2-NorpA vector is used for yeast expression of the NBC1 Aga2-NorpA.
Figure 13:
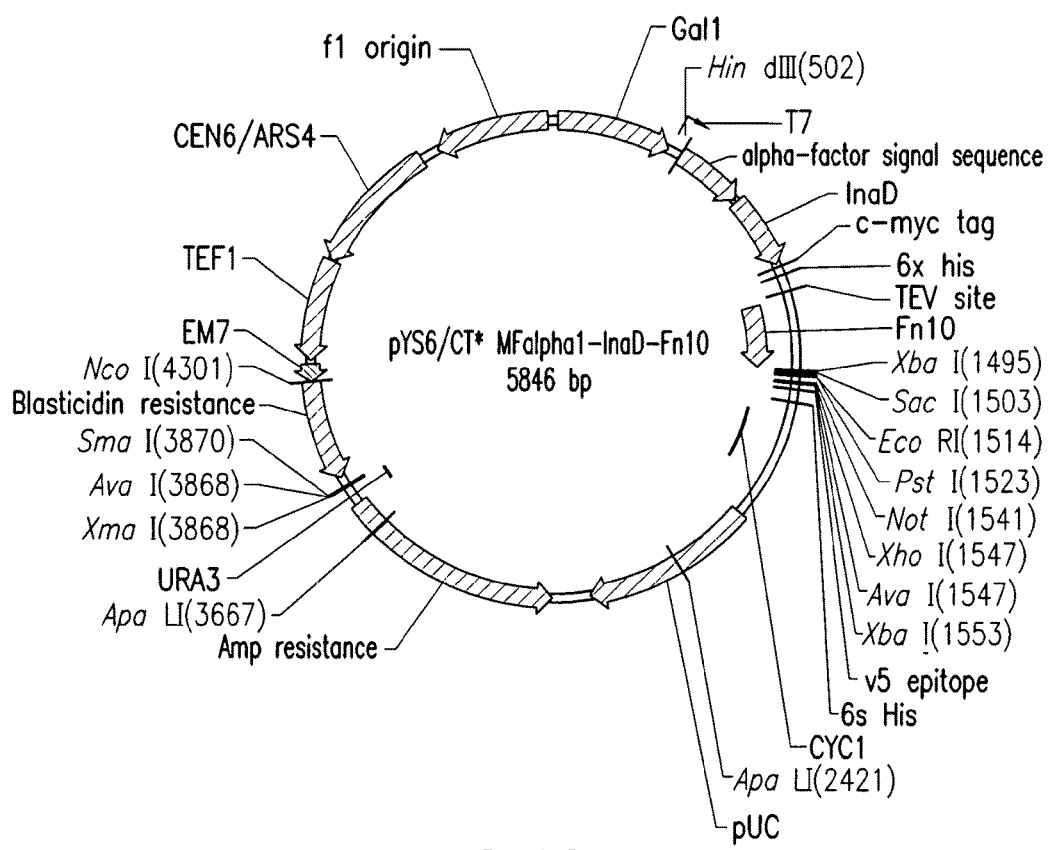
FIG. 13 shows a reversed system in which the pYS6/CT*MFalpha1-InaD-Fn10 vector is used for yeast expression of the MFalpha1-InaD-Fn10.

This example describes using the InaD/NorpA system with other yeast strains such as *Saccharomyces cerevisiae*
Strains and Media
*Escherichia coli* Top10 (Invitrogen, Carlsbad, Calif.) was used as the host strain for recombinant DNA manipulation. The *S. cerevisiae* strain EBY100 (Invitrogen Co., Carlsbad, Calif.) was used for the production of the fusion proteins AGA2-InaD and MSalpha1/HSA-Fn10-NorpA or pYS6CT*MFalpha1-HSA-NorpA. *E. coli* was cultivated in LB medium (1% tryptone, 0.5% yeast extract, and 0.5% sodium chloride) containing 100 ug/mL ampicillin or 100 ug/ml Blasticidin. EBY100 was cultivated in CM medium-URA.
Construction of Expression Plasmids
The InaD anchor gene was synthesized by Geneart (Germany) and subcloned in frame with the AGA2 anchor protein into the expression vector pYD NBC1 (derivative of pYD1Invitrogen) using HindIII and EcoRI restriction sites. The resulting vector was named pYD_NBC1 AGA2-InaD (FIG. 10). The fibronectin construct consists of the MFalpha1/HSA hybrid leader sequence followed by the fibronectin fused at its C-terminus to the NorpA ligand. The complete gene was synthesized by Geneart (Germany) and subcloned into pYS6CT (Invitrogen)), in which the origin of replication had been replaced by the CEN6/ARS4 region. The resulting vector was named pYS6CT_HSA_MFalpha1_Fn10_NorpA (FIG. 12).
Plasmids were isolated from *E. coli* and the sequence confirmed. The purified plasmids were then co-transformed into EBY100 and plated out on selective media consisting of CM-TRP, +200 ug/ml Blasticidin. Transformed colonies appeared within 2 days and were tested for display of Fibronectin by FACS analysis using an anti-myc antibody (ccccc).

Example 4: Yeast Display Using Flo1-InaD/NorpA in *Pichia pastoris*

This example describes the use of an alternative expression system, Flo1, which is used with InaD/NorpA in *Pichia pastoris*.
Strains and Media
The *Escherichia coli* Top10 strain (Invitrogen Carlsbad, Calif.) is used as the host strain for recombinant DNA manipulation. The *P. pastoris* GS115 strain (Invitrogen Co., Carlsbad, Calif.) is used for the production of the fusion protein Flo1-InaD and HSA/MFalpha1-Fn10-NorpA. *E. coli* was cultivated in LB medium (1% tryptone, 0.5% yeast extract, and 0.5% sodium chloride) containing 100 ug/mL ampicillin. *P. pastoris* was cultivated in BMGY medium (1% yeast extract, 2% peptone, 100 mM potassium phosphate buffer (pH 6.0), 1.34% yeast nitrogen base, $4\times10^{-5}$% biotin, and 1% glycerol), and BMMY medium (1% yeast extract, 2% peptone, 100 mM potassium phosphate buffer (pH 6.0), 1.34% yeast nitrogen base, $4\times10^{-5}$% biotin, and 0.5-2.0% methanol).
Construction of Expression Plasmids
The gene for Flo1, fused at the C-terminus to the PDZ domain of InaD, is synthesized by Geneart (Germany) and cloned into pPIC3.5 (Invitrogen) using a 5' EcoR1 site and a 3'NotI site. The resulting plasmid is named pPIC3.5-Flo1-InaD. Expression of the fused protein is driven by the methanol inducible promoter AOX1. The fibronectin construct consists of the MFalpha1/HSA hybrid leader followed by the fibronectin fused at the C-terminus to the NorpA ligand sequence. The complete gene is synthesized by Geneart (Germany) and subcloned into pPICHOLI-1 (Mobitec). The resulting vector is named pPICHOLI-1 MFalpha1Hsa-Fn10-NorpA. Expression of the fibronectin construct is driven by the methanol inducible promoter AOX1.
Yeast Transformation.
Electro-competent *P. pastoris* GS115 (Invitrogen) strain is prepared according to the protocol specified by the supplier and co-transformed with SalI-digested pPIC3.5-Flo1-InaD, and pPICHOLI-1 MFalpha1Hsa-Fn10-NorpA.
Cultivation Conditions
The yeast transformants are precultivated in BMGY medium containing 100 ug/ml Zeocin and 200 ug/ml Blasticidin at 30° C. for 16 hr. and used to inoculate 200 ml of BMGY medium (containing 100 ug/ml Zeocin and 200 ug/ml Balsticidin) in a 1 l baffle flask to give an initial $OD_{600}$ value of 0.1. After 24 hr. of cultivation, the culture is centrifuged at 1000 g for 10 min. and resuspended in BMMY medium (+100 ug/ml Zeocin and 200 ug/ml Blasticidin) containing 0.5%, 1.0%, or 2.0% methanol. To maintain the induction of the fusion proteins, 100% methanol is added every 24 hr. to the culture to the final concentrations mentioned above. Analysis of displayed fibronectins on the surface of yeast is performed using FACS and anti-myc antibody.

Example 5: Screening of a Fibronectin Library

Fibronectin Library Display
A fibronectin library is generated by methods well known in the art, including the method disclosed in U.S. Pat. No.

6,673,901. Other methods, such as use of error prone PCR, use of random priming techniques, or use of computational techniques are well known in the art and can also be used. The fibronectin library is designed with appropriate restriction enzyme cleavage sites in order to clone the library into yeast expression vectors.

The fibronectin library is displayed on a plurality of *P. pastoris* cells as described above in Example 1. The fibronectin library is modified to contain an MFalpha/HSA hybrid leader sequence fused to the N-terminus and a NorpA ligand sequence fused to the C-terminus. The modified fibronectin library is then cloned into the pPICHOLI-1 vector. As in the examples above, the expression of the fibronectin library is under the control of the AOX1 promoter. *P. pastoris* cells are transformed with the pPICHOLI-1 vectors expressing the fibronectin library and the vectors expressing Aga1p and Aga2p-InaD. Expression of the components is induced by the addition of methanol to the cells, and. the fibronectin library is displayed on a plurality of *P. pastoris* cells.

Screening of Display Library

The yeast display fibronectin library is screened for binding to a target protein of interest using one of many methods known in the art. For example, the target protein is contacted with the yeast display fibronectin library under conditions that allow for the specific binding of the target protein to any members of the library. All bound target protein is now immobilized on the surface of a yeast cell. All unbound target protein is washed off. The bound target protein is fluorescently labeled by methods well known in the art, such as fluorescently labeled antibodies specific for the target protein. The labeled target protein, now immobilized on the surface of a yeast cell, is then detected using flow cytometry, i.e. FACS. Yeast cells that bind the labeled target protein will fluoresce and are sorted from those yeast cells that do not bind the target protein. The sorted yeast cells that have bound the target protein are clonally expanded, and the clone line or line containing members of the fibronectin library that bind the target protein are determined.

Example 6: Screening of a Protein Library

Protein Library Display

A protein library is generated by methods well known in the art, such as use of error prone PCR, use of random priming techniques, or use of computational techniques. The protein library is designed with appropriate restriction enzyme cleavage sites in order to clone the library into yeast expression vectors.

The cloned protein library is displayed on a plurality of *P. pastoris* cells as described above in Example 1. The protein library is modified to contain an MFalpha/HSA hybrid leader sequence fused to the N-terminus and a NorpA ligand sequence fused to the C-terminus. The modified protein library is then cloned into the pPICHOLI-1 vector. As in the examples above, the expression of the protein library is under the control of the AOX1 promoter. *P. pastoris* cells are transformed with the pPICHOLI-1 vectors expressing the protein library and the vectors expressing Aga1p and Aga2p-InaD. Expression of the components is induced by the addition of methanol to the cells, and, the protein library is displayed on a plurality of *P. pastoris* cells.

Screening of Display Library

The yeast display protein library is screened for binding to a target protein of interest using one of many methods known in the art. For example, the target protein is contacted with the yeast display protein library under conditions that allow for the specific binding of the target protein to any members of the library. All bound target protein is now immobilized on the surface of a yeast cell. All unbound target protein is washed off. The bound target protein is fluorescently labeled by methods well known in the art, such as fluorescently labeled antibodies specific for the target protein. The labeled target protein, now immobilized on the surface of a yeast cell, is then detected using flow cytometry, i.e. FACS. Yeast cells that bind the labeled target protein will fluoresce and are sorted from those yeast cells that do not bind the target protein. The sorted yeast cells that have bound the target protein are clonally expanded, and the clone line or line containing members of the protein library that bind the target protein are determined.

Example 7: Screening of a Fibronectin or HSA Libraries

Fibronectin or HSA Library Display

A fibronectin or HSA library is generated by methods well known in the art, such as use of error prone PCR, use of random priming techniques, or use of computational techniques. The libraries are designed with appropriate restriction enzyme cleavage sites in order to clone the libraries into yeast expression vectors (See FIG. 8 and SEQ ID NO: 10).

The cloned fibronectin library or HSA library is displayed on a plurality of *P. pastoris* cells as described above in Example 1. The fibronectin library is modified to contain an MFalpha/HSA hybrid leader sequence fused to the N-terminus and a NorpA ligand sequence fused to the C-terminus (pYS HSA_MFalpha1 Fn10 NorpA). The HSA library is modified to contain a MFalpha CT (C-Terminal) It is a left-over of the original Invitrogen vector used for the constructions. If you look at the vector map (e.g. FIG. 13) you can see a c-terminal v5 and 6×his sequence of the c-terminus of the insert. I've placed a stop in front of it and it is not translated in the final displayed protein. leader sequence (pYS6/CT HSA-NorpA). The modified fibronectin or HISA library is then cloned into the pYS vector. The expression of the fibronectin or HSA library is under the control of the T7 promoter. *P. pastoris* cells are transformed with the pYS vectors expressing the fibronectin or HSA library and the vectors expressing Aga1p and Aga2p-InaD. Expression of the components is induced by the addition of methanol to the cells, and. the fibronectin or HSA library is displayed on a plurality of *P. pastoris* cells.

(a) FACS Analysis of Protein Surface Expression.

Figure 9A:
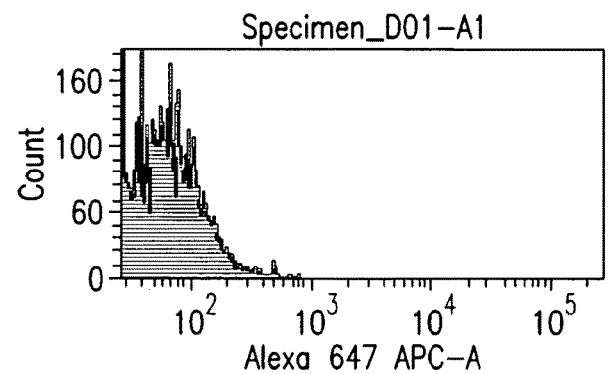
FIG. 9A-E are FACS analysis graphs showing protein surface expression of yeast cells expressing either fibronectin (pYS6/CT HSA MFalpha1 Fn10 NorpA) or HSA (pYS6/CT MFalpha1-HISA-NorpA) in which the yeast cells are stained with anti-myc antibody and APC labeled secondary anti-mouse antibody.
Figure 9B:
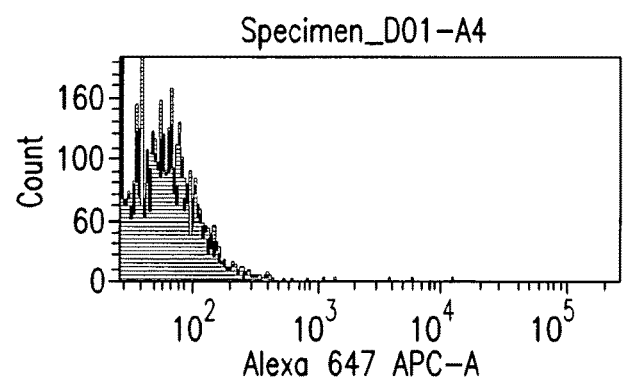
Figure 9C:
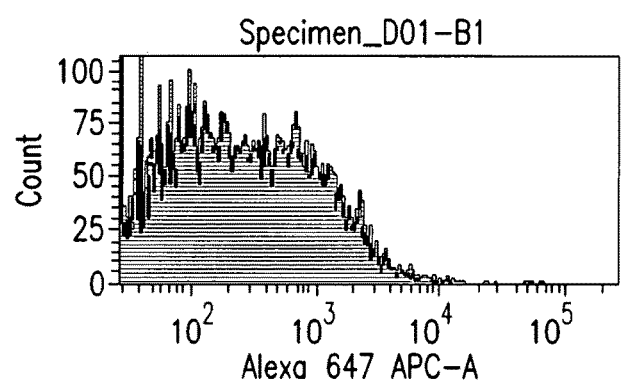
Figure 9D:
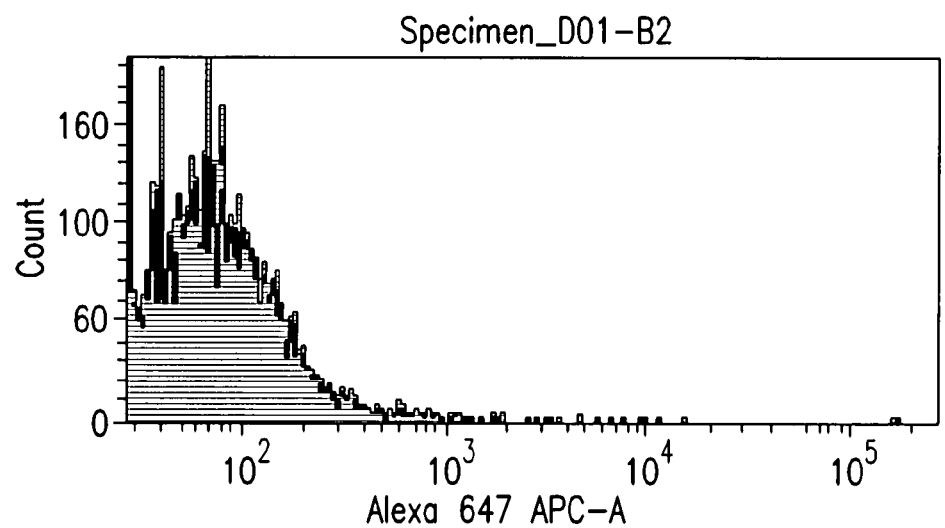
Figure 9E:
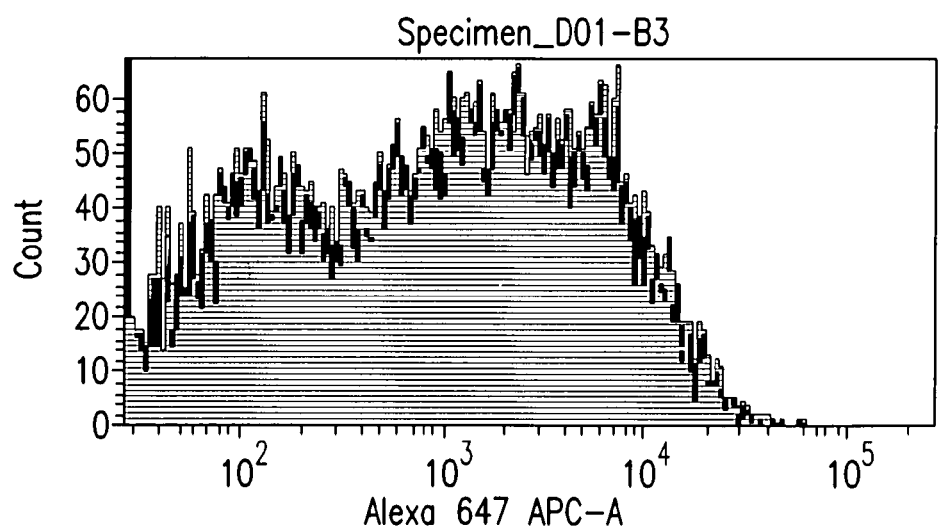

Yeast cells expressing either fibronectin (pYS HSA_MFalpha1 Fn10 NorpA) or HISA (pYS6/CT HSA-NorpA) were stained with anti-myc antibody, followed by APC labeled secondary anti-mouse antibody and then subjected to FACS analysis. The results of the analysis are shown in FIGS. 9A-E. Specifically, FIG. 9A is the control sample showing unstained yeast cells; FIG. 9B is a sample of uninduced yeast cells expressing fibronectin; FIG. 9C is a sample of induced yeast cells expressing fibronectin, showing a shift of cells compared with the uninduced cells; FIG. 9D is a sample of uninduced yeast cells expressing HSA; and FIG. 9E is a sample of induced yeast cells expressing HSA, again showing a shift of cells compared with the uninduced cells. These results clearly demonstrate that the yeast display system is able to express fibronectin molecules, and proteins, such as HSA.

Figure 10A:
FIG. 10A-E are images of FMAT analysis of yeast cells expressing either fibronectin (pYS6/CT HSA MFalpha1 Fn10 NorpA) or HSA (pYS6/CT HSA-NorpA) in which the yeast cells are stained with anti-myc mouse monoclonal antibody and APC labeled secondary anti-mouse antibody and subjected to FMAT confocal fluorescence.
Figure 10B:
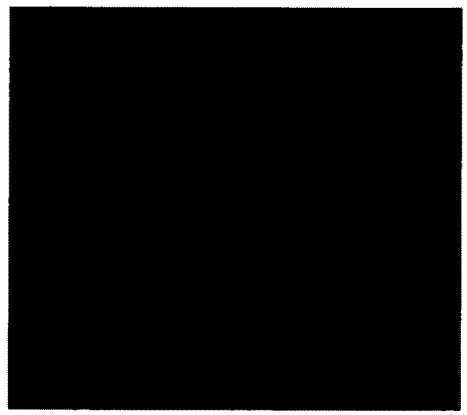
Figure 10C:
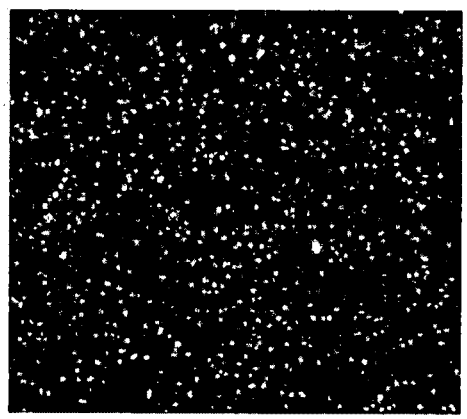
Figure 10D:
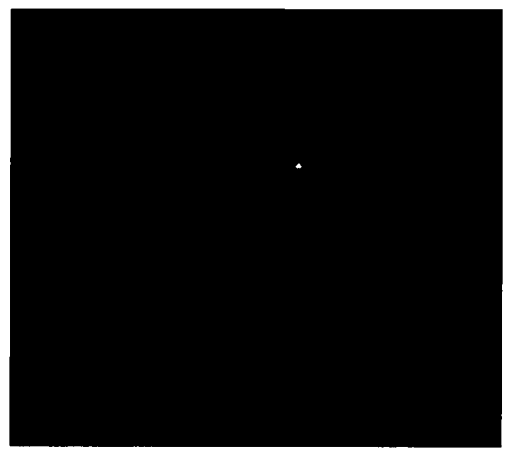
Figure 10E:
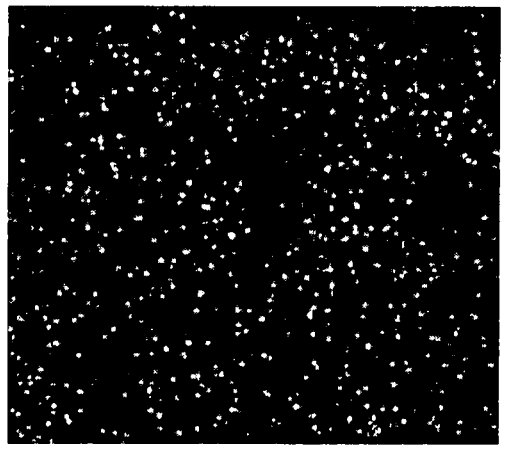

(b) Fluorometric Microvolume Assay Technology (FMAT, Perkin Elmer) Analysis of Yeast Expressing Fibronectin or HSA Yeast cells expressing either fibronectin (plasmid) or HISA (plasmid) were also analyzed by FMAT by staining with anti-myc antibody and APC labeled secondary anti-mouse antibody. The samples were then subjected to FMAT confocal fluorescence microscopy and shown in FIGS. 10A-E. Those colonies that express fibronectin or HSA appear as white dots against a black background. Specifically, FIG. 10A is the control sample showing unstained yeast cells and appears entirely black; FIG. 10B is a sample of uninduced yeast cells expressing fibronectin. The uninduced yeast cells do not produce fibronectin and are not detected (image appears black); FIG. 10C is a sample of induced yeast cells expressing fibronectin. In this instance, induction leads to the fibronectin with a myc tag being expressed and detected using the anti-myc antibody. Subsequent detection with the APC secondary anti-mouse antibody and FMAT confocal fluorescence microscopy results in visible white colonies being detected. FIG. 10D is a sample of uninduced yeast cells expressing HSA, as before the uninduced yeast cells do not produce fibronectin and the image appears black; and FIG. 10E is a sample of induced yeast cells expressing HSA, again showing small white colonies compared with the uninduced cells. These results further confirm that the yeast display system is able to express fibronectin molecules, and proteins, such as HSA.

Example 8: Screening of Single Chain Fv Libraries

Single Chain Fv Library Display

Figure 11:
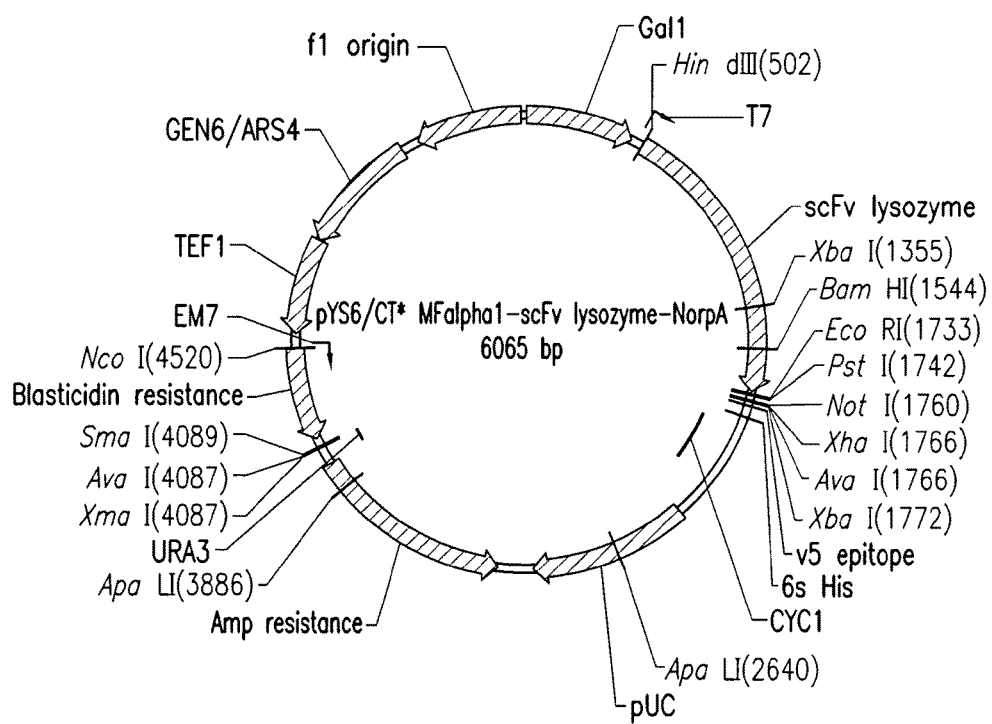
FIG. 11 shows the pYS MFalpha1 scFv lysozyme NorpA vector for yeast expression of the MFalpha1 scFv lysozyme NorpA fusion polypeptide as the display molecule where the NorpA is the binding partner of the second binding site of the adapter molecule (i.e., InaD) and the lysozyme is modified polypeptide.

A single chain Fv library is generated by methods well known in the art, such as use of error prone PCR, use of random priming techniques, or use of computational techniques. The libraries are designed with appropriate restriction enzyme cleavage sites in order to clone the libraries into yeast expression vectors (See FIG. 11 and SEQ ID NO: 11).

The cloned scFv lysozyme library is displayed on a plurality of P. pastoris cells as described above in Example 1. The scFv library is modified to contain an MFalpha leader sequence fused to the N-terminus and a NorpA ligand sequence fused to the C-terminus (pYS6/CT* MFalpha1-scFv lysozyme-NorpA). The modified scFv lysozyme library is then cloned into the pYS vector. The expression of the scFv lysozyme is under the control of the T7 promoter. P. pastoris cells are transformed with the pYS vectors expressing the scFv lysozyme library and the vectors expressing Aga1p and Aga2p-InaD. Expression of the components is induced by the addition of methanol to the cells, and. the fibronectin or HSA library is displayed on a plurality of P. pastoris cells.

(a) FACS Analysis of Protein Surface Expression.

Yeast cells expressing the scFv lysozyme were stained with anti-myc antibody, followed by APC labeled secondary anti-mouse antibody and then subjected to FACS analysis.

(b) FMAT Analysis of Yeast Expressing Fibronectin or HSA

Yeast cells expressing the scFv lysozyme were also analyzed by FMAT by staining with anti-myc antibody and APC labeled secondary anti-mouse antibody. The samples were then subjected to FMAT confocal fluorescence microscopy.

Example 9: Screenshot of Protein Libraries with a Reverse System

Protein Library Display

In the Example, the yeast display system described herein is reversed such that NorpA is fused to Aga2 and the InaD is fused to Aga1. A protein library is generated by methods well known in the art, such as use of error prone PCR, use of random priming techniques, or use of computational techniques. The libraries are designed with appropriate restriction enzyme cleavage sites in order to clone the libraries into yeast expression vectors (See FIGS. 12 and 13 and SEQ ID NOs: 12 and 13).

The protein display system for P. pastoris was developed to display a fibronectin type III domain (Fn10), by fusing a leader sequence (MFalpha1) at N-terminus of InaD and fusing the Fn10 to its C-terminus. Once expressed, the Fn10 was secreted from the cell and the PDZ domain of InaD bound to the NorpA ligand through disulfide bonds. The NorpA was fused to the C-terminus of the Agap2 protein. The Aga2p-NorpA fusion protein served as the adapter protein, and the N-terminal Aga2p bound Aga1p, which was immobilized on the surface of the cell. Aga2p bound specifically to Aga1p through disulfide bonds.

The three component system consisting of the Aga2p-NorpA fusion protein, the Aga1-InaD fusion protein, and the Aga1p cell surface protein were cloned into pPD and pYS expression vectors respectively, under the control of a Gal inducible promoter.

The inducible promoter used was the Gal1 promoter, which is induced by galactose. Thus when galactose was added to yeast cells transformed with the vectors, the three proteins were expressed. Aga1p was expressed on the surface of the cell. Aga2p-Norp was localized to the cell surface where the N-terminal region of Aga2p-NorpA bound to Aga1p. Fn10-InaD was localized to the secretory pathway, was secreted from the cell, and bound NorpA via the C-terminal InaD ligand.

SEQUENCES

```
pPIC3.5 AGA1 (956 bp-3136 bp, direct) 242aa
MTLSFAHFTY  LFTILLGLTN  IALASDPETI  LVTITKTNDA  NGVVTTTVSP
ALVSTSTIVQ  AGTTTLYTTW  CPLTVSTSSA  AEISPSISYA  TTLSRFSTLT
LSTEVCSHEA  CPSSSTLPTT  TLSVTSKFTS  YICPTCHTTA  ISSLSEVGTT
TVVSSSAIEP  SSASIISPVT  STLSSTTSSN  PTTTSLSSTS  TSPSSTSTSP
SSTSTSSSST  STSSSSTSTS  SSSTSTSPSS  TSTSSSLTST  SSSSTSTSQS
STSTSSSSTS  TSPSSTSTSS  SSTSTSPSSK  STSASSTSTS  SYSTSTSPSL
TSSSPTLAST  SPSSTSISST  FTDSTSSLGS  SIASSSTSVS  LYSPSTPVYS
VPSTSSNVAT  PSMTSSTVET  TVSSQSSSEY  ITKSSISTTI  PSFSMSTYFT
TVSGVTTMYT  TWCPYSSESE  TSTLTSMHET  VTTDATVCTH  ESCMPSQTTS
LITSSIKMST  KNVATSVSTS  TVESSYACST  CAETSHSYSS  VQTASSSSVT
QQTTSTKSWV  SSMTTSDEDF  NKHATGKYHV  TSSGTSTIST  SVSEATSTSS
IDSESQEQSS  HLLSTSVLSS  SSLSATLSSD  STILLFSSVS  SLSVEQSPVT
TLQISSTSEI  LQPTSSTAIA  TISASTSSLS  ATSISTPSTS  VESTIESSSL
TPTVSSIFLS  SSSAPSSLQT  SVTTTEVSTT  SISIQYQTSS  MVTISQYMGS
GSQTRLPLGK  LVFAIMAVAC  NVIFS  (SEQ ID NO: 2)
```

SEQUENCES pPIC6 A AGA2-InaD (941 bp-1648 bp, direct) 78aa
MQLLRCPSIF SVIASVLAQE LTTICEQIPS PTLESTPYSL STTTILANGK
AMQGVFEYYK SVTFVSNCGS HPSTTSKGSP INTQYVFKLL QASGGGGSGG
GGSGGGGSAS MTGGQQMGRE NLYFQGVPGS SVVSRAGELI HMVTLDKTGK
KSFGICIVRG EVKDSPNTKT TGIFIKGIVP DSPAHLCGRL KVGDRILSLN
GKDVRNSTEQ AVIDLIKEAD FKIELEIQTF DK (SEQ ID NO: 3)

pPICHOLI-1_MFalpha1Hsa-Fn10-NorpA (884 bp-1441 bp, direct) 62aa
MKWVSFISLL FLFSSAYSRS LDKRENLYFQ GGSVSDVPRD LEVVAATPTS
LLISWDAPAV TVRYYRITYG ETGGNSPVQE FTVPGSKSTA TISGLKPGVD
YTITVYAVTG RGDSPASSKP ISINYRTEFE NLYFQGSGGG GEQKLISEED
LHHHHHHPST PPTPSPSTPP TPSPSYKTQG KTEFCA (SEQ ID NO: 4)

pPICHOLI-C MfalphalHsa-Fn10-NorpA (691 bp-1248 bp, direct) 62aa
MKWVSFISLL FLPSSAYSRS LDKRENLYFQ GGSVSDVPRD LEVVAATPTS
LLISWDAPAV TVRYYRITYG ETGGNSPVQE FTVPGSKSTA TISGLKPGVD
YTITVYAVTG RGDSPASSKP ISINYRTEFE NLYFQGSGGG GEQKLISEED
LHHHHHHPST PPTPSPSTPP TPSPSYKTQG KTEFCA (SEQ ID NO: 5)

pYD_NBC1_Aga2-InaD (534 bp-1235 bp, direct) 78aa
MQLLRCFSIF SVIASVLAQE LTTICEQIPS PTLESTPYSL STTTILANGK
AMQGVFEYYK SVTFVSNCGS HPSTTSKGSP INTQYVFKLL QASGGGGSGG
GGSGGGGSAS MTGGQQMGRE NLYFQGVPGS SVVSRAGELI RMVTLDKTGK
KSFGICIVRG EVKDSPNTKT TGIFIKGIVP DSPAHLCGRL KVGDRILSLN
GKDVRNSTEQ AVIDLIKEAD FKIELEIQTF DK (SEQ ID NO: 6)

pYS6/CT_HSA_MFalpha1_Fn10_NorpA (513 bp-1080 bp, direct) 63aa
MKWVSFISLL FLFSSAYSRS LDKRENLYFQ GGSVSDVPRD LEVVAATPTS
LLISWDAPAV TVRYYRITYG ETGGNSPVQE FTVPGSKSTA TISGLKPGVD
YTITVYAVTG RGDSPASSKP ISINYRTEFE NLYFQGSGGG GEQKLISEED
LHHHHHHPST PPTPSPSTPP TPSPSYKTQG KTEFCA (SEQ ID NO: 7)

InaD PDZ domain amino acid sequence (InaD aa 11-107)
AGELIHMVTL DKTGKKSFGI CIVRGEVKDS PNTKTTGIFI KGIVPDSPAH
LCGRLKVGDR ILSLNGKDVR NSTEQAVIDL IKEADFKIEL EIQTFDK (SEQ ID NO: 8)

NorpA C-terininal 11 amino acids including EFCA motif
YKTQGKTEFC A (SEQ ID NO: 9)

pYS6/CT* MFalpha HSA-NorpA
MRFPSIFTAVLFAASSALAAPVNTTTEDETAQIPAEAVIGYSDLEGDFDVAVLPFSNST
NNGLLFINTTIASIAAKEEGVSLEKREAEAASDAHKSEVAERFKDLGEENFKALVLIAF
AQYLQQCPFEDHVKLVNEVTEFAKTCVADESAENCDKSLHTLFGDKLCTVATLRETYGE
MADCCAKQEPERNECFLQHKDDNPNLPRLVRPEVDVMCTAFHDNEETFLKKYLYEIARR
HPYFYAPELLFFAKRYKAAFTECCQAADKAACLLPKLDELRDEGKASSAKQRLKCASLQ
KFGERAFKAWAVARLSQRFPKAEFAEVSKLVTDLTKVHTECCHGDLLECADDRADLAKY
ICENQDSISSKLKECCEKPLLEKSHCIAEVENDEMPADLPSLAADFVESKDVCKNYAEA
KDVFLGMFLYEYARRHPDYSVVLLLRLAKTYETTLEKCCAAADPHECYAXVFDEFKPLV
EEPQNLIKQNCELFEQLGEYKPQNALLVRYTKKVPQVSTPTLVEVSRNLGKVGSKCCKH
PEAKRMPCAEDYLSVVLNQLCVLHERTPVSDRVTKCCTESLVNRRPCFSALEVDETYVP
KEFNAETFTFHADICTLSEKERQIKKQTALVELVKHKPKATKEQLKAVMDDFAAFVEKC
CKADDKETCFAEEGKKLVAASQAALGLGSENLYFQGSGGGGEQKLISEEDLRHHHHHHH
PSTPPTPSPSTPPPTPSPSYKTQGKTEFCA (SEQ ID NO: 10)

pYS6/CT* MFalpha1-scFv lysozyme-NorpA
MRFPSIFTAVLFAASSALAAPVNTTTEDETAQIPAEAVIGYSDLEGDFDVAVLPFSNS
TNNGLLFINTTIASIAAKEEGVSLEKREAEAASQVKLQQSGAELVKPGASVKLSCTASG
FNIKDTYMHWVKQRPEQGLEWIGRIDPANGNTKYDPKFQGKATITADTSSNTAYLQLSS
LTSEDTAVYYCARWDWYFDVWGQGTTVTVSSGGGGSGGGGSGGGGSDIELTQSPSSMYT
SLGERVTITCKASQDINSYLRWFQQKPGKSPKTLIYYATSLADGVPSRFSGSGSGQDYS
LTISSLESDDTTTYYCLQHGESPYTFGGGTKLEIKRAAAEQKLISEEDLNGSENLYFQG
SGGGGEGKLISEEDLHHHHHHHHPSTETTPSPSTEPTPSPSYKTQGKTEFCA (SEQ ID NO: 11)

pYD_NBC1_Aga2-NorpA
MQLLRCSIFSVIASVLAQELTTICEQIPSPTLESTETSLSTTTILANGKAMQGVFEYY
KSVTFVSNCGSHPSTTSRGSPINTQYVFKLLQASGGGGSGGGGSYKTQGKTEFCA
(SEQ ID NO: 12)

pYS6/CT* MFalpha1-InaD-Fn10 (507 bp-1487 bp, direct) 109aa
MRFPSIFTAVLFAASSALAAPVNTTTEDETAQIPAEAVIGYSDLEGDFDVAVLPFSNST
NNGLLFINTTIASIAAKEEGVSLEKREAEAASAGELIHMVTLDKTGKKSFGICIVRGEV
KDSPNTKTTGIFIKGIVPDSPAHLCGRLKVGDRILSLNGKDVRNSTEQAVIDLIKEADF
KIELEIQTFDKSGGGGEQKLISEEDLHHHHHHPSTPPTPSPSTPPTSPENLYFQGVSD
VPRDLEVVAATPTSLLISWDAPAVTVRYYRITYGETGGNSPVQEFTVPGSKSTATISGL
KPGVDYTITVYAVTGRGDSPASSKPISINYRT (SEQ ID NO: 13)

I claim:

1. A method for displaying a modified polypeptide for screening for binding to a target comprising:
   (a) providing an adapter molecule comprising a first binding site and a second binding site and a host cell comprising a cell surface molecule attached to the surface of the cell which is expressed from an expression vector in the host cell and a first nucleic acid encoding a display molecule comprising a modified polypeptide and a binding partner for the second binding site of the adapter molecule, wherein the modified polypeptide is an immunoglobulin,
   (b) contacting the host cell with the adapter molecule under conditions wherein the first binding site of the adapter molecule binds to the cell surface molecule, and
   (c) incubating the host cell under conditions wherein the host cell exports the display molecule outside the host cell under conditions wherein the second binding site of the adaptor molecule binds to the display molecule,
   wherein the first binding site of the adapter molecule binds specifically to the cell surface molecule and cannot bind to the display molecule, and the second binding site of the adaptor molecule binds specifically to the display molecule and cannot bind to the cell surface molecule,
   wherein the adapter molecule is not a component of the modified polypeptide,
   wherein the adapter molecule does not bind to any fragment of the modified polypeptide by immunoglobulin light chain binding to immunoglobulin heavy chain, and
   wherein (i) the host cell surface molecule is covalently linked to the first binding site of the adapter molecule or (ii) the second binding site of the adapter molecule is covalently linked to the display molecule or (iii) the host cell surface molecule is covalently linked to the first binding site of the adapter molecule and the second binding site of the adapter molecule is covalently linked to the display molecule.

2. The method of claim 1, wherein the host cell displays at least $10^2$, at least $10^3$, at least $10^4$, or at least $10^5$ modified polypeptides.

3. The method of claim 1, wherein the cell surface molecule is covalently linked to the first binding site of the adaptor molecule.

4. The method of claim 1, wherein the cell surface molecule is covalently linked to the first binding site of the adaptor molecule through a disulfide bond.

5. The method of claim 1, wherein the cell surface molecule comprises a first agglutinin.

6. The method of claim 5, wherein the first agglutinin is Aga1p.

7. The method of claim 1, wherein the cell surface molecule is attached to the host cell membrane via a GPI anchor.

8. The method of claim 5, wherein the first binding site of the adaptor molecule comprises a second agglutinin.

9. The method of claim 8, wherein the second agglutinin is Aga2p.

10. The method of claim 1, wherein the second binding site of the adaptor molecule is covalently linked to the display molecule.

11. The method of claim 1, wherein the second binding site of the adaptor molecule is covalently linked to the display molecule through disulfide bonds.

12. The method of claim 1, wherein the second binding site of the adaptor molecule comprises a PDZ domain.

13. The method of claim 12, wherein the PDZ domain is the PDZ domain of InaD.

14. The method of claim 12, wherein the display molecule comprises a C-terminal NorpA ligand.

15. The method of claim 1, wherein the display molecule comprises a PDZ domain.

16. The method of claim 15, wherein the PDZ domain is the PDZ domain of InaD.

17. The method of claim 15, wherein the second binding site of the adaptor molecule comprises a C-terminal NorpA ligand.

18. The method of claim 1, wherein the display molecule comprises a secretion signal peptide.

19. The method of claim 18, wherein the secretion signal peptide comprises an MFalpha/HSA hybrid leader peptide.

20. The method of claim 18, wherein the secretion signal peptide comprises an MFalpha leader peptide.

21. The method of claim 1, wherein expression of the display molecule is under the control of a first inducible promoter.

22. The method of claim 21, wherein the first inducible promoter is selected from the group consisting of an AOX 1 promoter and a Cup 1 promoter.

23. The method of claim 21, wherein the first inducible promoter is a Gal 1 promoter.

24. The method of claim 21, wherein the expression of the adapter molecule is under the control of a second inducible promoter.

25. The method of claim 24, wherein the second inducible promoter is selected from the group consisting of an AOX 1 promoter and a Cup 1 promoter.

26. The method of claim 24, wherein the second inducible promoter is a Gal 1 promoter.

27. The method of claim 1, wherein the host cell is a yeast cell.

28. The method of claim 27, wherein the yeast cell is selected from the group consisting of: *Pichia pastoris* and *Saccharomyces cerevisiae*.

* * * * *